US005821227A

United States Patent [19]
Dennis et al.

[11] Patent Number: 5,821,227
[45] Date of Patent: Oct. 13, 1998

[54] MODULATORS OF CYTOKINES OF THE TGF β SUPERFAMILY

[75] Inventors: James W. Dennis, Etobicoke; Michael Demetriou, Toronto, both of Canada

[73] Assignee: Mount Sinai Hospital Corporation, Toronto, Canada

[21] Appl. No.: 483,926

[22] Filed: Jun. 7, 1995

Related U.S. Application Data

[63] Continuation of Ser. No. 237,715, May 4, 1994, abandoned.

[51] Int. Cl.$^6$ ........................... C07K 14/47; A61K 38/04
[52] U.S. Cl. .................................... 514/12; 514/2; 514/8; 530/350
[58] Field of Search ............................. 530/350; 514/2, 514/8, 12, 885

[56] References Cited

FOREIGN PATENT DOCUMENTS

| 2002011 | 5/1990 | Canada . |
| PCT/US91/ 04449 | 12/1991 | WIPO . |
| PCT/US92/ 03825 | 11/1992 | WIPO . |

OTHER PUBLICATIONS

Massague, J., 1990, Annu. Review Cell Biol. 6:597–641.
Ewen, M.E. et al., Cell 74, 1009–1020, 1993.
Knoff, A. et al., Science 260, 536–539, 1993.
Silberstein, G. and Daniel, W.D., Science 237:291–293, 1987.
Russell, W.E. et al., 1988, Proc. Natl. Acad. Sci USA 85:5126–5130.
Roberts, A.B. et al., Proc. Natl. Acad. Sci. USA, 78(9):5339–5343, 1981.
Roberts, A.B. et al., Nature 295:417–419, 1982.
Twardzik, D.R. and Sherwin, S.A., J. Cell. Biochem. 28:289–297, 1985.
Tucker, R.F. et al., Science 226:705–707, 1984.
Sporn, M.B. et al., Science 219:1329–1331, 1983.
Roberts, A.B. et al., Proc. Natl. Acad. Sci USA 83:4167–4171, 1986.
Mustoe, T.A. et al., Science 237:1333–1336, 1987.
Kehrl, J.H. et al., J. Immunol. 137:3855–3860, 1986.
Kehrl, J.H. et al., 1986, J. Exp. Med. 163:1037–1050.
Ristow, H.J., 1986, PNAS USA83:5531–5533.
Lotz, M. and Seth, P., Annals New York Acadamy of Science 685:501–511, 1993.
Baecher–Allan, C.M. and Barth, R.K., Regional Immunology 5(3–4):207–217, 1993.
Burt, A.D., J. of Pathology 170:105–114, 1993.
Anscher, M.S. et al., N. Engl. J. Med. 328(22):1592–1598, 1993.
Border, W.A. et al., Nature 360:361–364, 1992.
Martin, M. et al., Radiation Research 134:63–70, 1993.
Connor, B. et al., J. Clin Invest 83:1661–1666, 1989.
Kulozik,M. et al., J. Clin. Invest. 86;917–922, 1990.
Rosen, V. and Thies, R.S., Trends in Genetics, 8(3):97–102, 1992.

Padgett, R.W. et al., 1987, Nature, 325:81–84.
Mason, A.J. et al., 1985, Nature 318:659–663.
Ling, N. et al., Nature 321:779–782, 1986.
Cate, R.L. et al., Cell 45:685–698, 1986.
Massague, J., Cell, 69:1067–1070, 1992.
Lin, H. Y. et al., Cell 68:775–785, 1992.
Schultz–Cherry, S. and Murphy–Ulllrich, J.E. Cell Biol. 122(4)m 923–932 (1993).
Massague, J., Curr. Biol. 1(20, 117–119 (1991).
Yamaguchi, Y. et al., Nature 346:281–284, 1990.
Kellermann, J. et al., J. Biol. Chem. 264(24):14121–14128, 1989.
Puck, T.T. et al., Proc. Natl. Acad. Sci. USA 59, 192–199 (1968).
Daveau, M. et al., FEBS Lett. 273(1, 2), 79–81 (1990).
Dickson, I.R., Poole, A.R., Veis, A., Nature 256, 430–432 (1975).
Triffitt, J.T., Gebauer, U., Ashton, B.A., Owen, M.E., Nature 262, 226–227 (1976).
Rauth, G. et al., Eur. J. Biochem. 204, 523–529 (1992).
Colclasure, G.C. et al., J. Clin. Endocrin. Metabolism 66(1), 187–192 (1988).
Cayatte, A.J., Kumbla, L., Subbiah, M.T.R., J. Biol. Chem. 265(10), 2883–5888 (1990).
Basler, K. et al. Cell, 73:687–702, 1993.
Frolik, C.A. et al., 1983, Proc. Natl. Acad. Sci. USA 80:3676–3680.
Roberts, A.B. et al., 1983, Biochemistry 22:5692–5698.
Childs, C.B. et al., 1982, Proc. Natl. Acad. Sci. USA 79:5312–5316.
Kellermann, J. et al., Biochem. J. 247:15–21, 1987.
Farmer, P.S., in Drug Design, EJ Ariens, Ed. (Academic Press, New York, 1980) vol. 10, pp. 119–143.
Ball, J.B. and Alewood, P.F., J. Mol. Recognition 3:55, 1990.
Morgan, B.A. and Gainer, J.A., Annu. Rep. Med. Chem. 24, Chpter. 26, 243–252, 1989.
Friedinger, R.M., Trends Pharmacol. Sci. 10, 270–274, 1989.

(List continued on next page.)

*Primary Examiner*—John Ulm
*Assistant Examiner*—Perma Mertz
*Attorney, Agent, or Firm*—Merchant, Gould, Smith, Edell, Welter & Schmidt

[57] ABSTRACT

The invention relates to a method for assaying for the presence of a substance that modulates a cytokine of the TGFβ superfamily. A substance which is suspected of modulating a cytokine of the TGFβ superfamily and a TGFβ binding compound which is not a TGFβ receptor and which contains a TRH1 domain, or a portion or mimetic thereof, is reacted with a cytokine of the TGFβ superfamily under conditions where the compound, portion or mimetic thereof, and the cytokine are capable of forming a complex. Complexes, free compound and/or cytokine are assayed and compared with a control. The invention also relates to a composition comprising at least one compound which is not a TGFβ receptor and which contains the TRH1 domain or a portion, or a mimetic thereof, and a pharmaceutically acceptable carrier, auxiliary or excipient and to methods of treatment using the composition. Further the invention relates to a method of enhancing the activity of growth factors.

5 Claims, 11 Drawing Sheets

OTHER PUBLICATIONS

Merrifield, R.B., 1963, J. Am. Chem. Assoc. 85:2149–2154.

Wozney, J.M., et al., Science 242, 1528–1534 (1988).

L. Mercken, M. –J. Simons, S. Swillons, M. Massaer, G. Vassart, Nature 316, 647–651 (1985).

R. Ebner, R. –H. Chen, L. Shum, S. Lawler, T.F. Zioncheck, et al., Science 260, 1344–1348, 1993.

L. Attisano, J. Carcamo, F. Ventura, F.M.B. Weis, J. Massague, et al., Cell 75, 671–680 (1993).

P. Franzen, P. ten Dijke, H. Ichigo, H. Yamashita, P. Schulz, et al., Cell 75, 681–692 (1993).

C.H. Bassing, J.M. Yingling, D.J. Howe, T. Wang, W.W. He, et al., Science 263, 87–89 (1994).

J.L. Wrana, L. Attisano, J. Carcamo, A. Zentella, J. Doody, et al., Cell 71, 1003–1014 (1992).

McDonald, N.Q. and Hendrickson, W.A., Cell 73:421–242, 1993.

Demura, R. et al. Biochem. Biophys. Res. Com. 185(3):1148–1154, 1992.

Ashton, BA, Smith R., Clinical Science 1980;58:435–438.

Coletta, G., Cirafici, A.M., Di Carlo, A., Cancer Research, 1989; 49:3457–3462.

Lebreton, J.P., Joisel, F., J. Clin. Invest., 1979; 64:1118–1129.

O'Connor–McCourt, M.D., Wakefield, L.M., The J. Biol. Chem., 1987; 262(29):14090–14099.

Dziegielewska, K.M. et al., "The Complete cDNA and Amino Acid Sequence of Bovin Fetuin", The Journal of Biological Chemistry, vol. 26, 8:4354–4357, 1990.

Begbie et al. (1974) Biochimica et Biophynica Acta, 371, pp. 549–567.

Smith et al. (1987) Science, vol. 238, pp. 1704–1707.

Lin et al. (1992) Cell, vol. 68, pp. 775–785.

```
                                    TRH1
mTGF-betaRI     CGNED--HCEGQKCFSSLSIYDGFHVYQK----------------GCFQ  72
hTGF-betaRII    CDNQK--SCMS-NC-SITSICEKPQEVC-VAVWRKNDEN-IT-LETVCHD 103
bTHYROGLOBULIN  CSADYSGLLLAFQVFLLDELT-A-RGFCQIQV---KTAGTPVS-I-PVCDD 1349
bFETUIN         CHVLDPTP-LA-NCSVRQQTQHAVEGDCDIHVL-KQDGQ-FSVLFTKC-D  133
                         a                          b
```

FIG. 11

TRANSLATE of: m85079.gb_pr check: 1576 from: 336 to 2036 generated symbols 1 to: 567

LOCUS       HUMTGFBIIR    2090 bp   ss-mRNA    PRI 31-JUL-1992
DEFINITION  Human TGF-beta type II receptor mRNA, complete cds.
ACCESSION   M85079
KEYWORDS    TGF-beta type II receptor.
SOURCE      Homo sapiens (library: lambda zapII) cDNA to mRNA.
  ORGANISM  Homo sapiens tyII.pep    Length: 567  October 12, 1993  14:39  Type: P
Check: 5743 ..

1    MGRGLLRGLW PLHIVLWTRI ASTIPPHVQK SVNNDMIVTD NNGAVKFPQL

51   CKFCDVRFST CDNQKSCMSN CSITSICEKP QEVCVAVWRK NDENITLETV

101  CHDPKLPYHD FILEDAASPK CIMKEKKKPG ETFFMCSCSS DECNDNIIFS

151  EEYNTSNPDL LLVIFQVTGI SLLPPLGVAI SVIIIFYCYR VNRQQKLSST

201  WETGKTRKLM EFSEHCAIIL EDDRSDISST CANNINHNTE LLPIELDTLV

251  GKGRFAEVYK AKLKQNTSEQ FETVAVKIFP YEEYASWKTE KDIFSDINLK

301  HENILQFLTA EERKTELGKQ YWLITAFHAK GNLQEYLTRH VISWEDLRKL

351  GSSLARGIAH LHSDHTPCGR PKMPIVHRDL KSSNILVKND LTCCLCDFGL

401  SLRLDPTLSV DDLANSGQVG TARYMAPEVL ESRMNLENAE SFKQTDVYSM

451  ALVLWEMTSR CNAVGEVKDY EPPFGSKVRE HPCVESMKDN VLRDRGRPEI

501  PSFWLNHQGI QMVCETLTEC WDHDPEARLT AQCVAERFSE LEHLDRLSGR

551  SCSEEKIPED GSLNTTK

MODULATORS OF CYTOKINES OF THE TGF β SUPERFAMILY

CROSS REFERENCE TO RELATED APPLICATION

This is a continuation of U.S. patent application Ser. No. 08/237,715, filed May 4, 1994, now abandoned.

FIELD OF THE INVENTION

The present invention relates to methods and compositions for treating conditions requiring modulation of cytokines of the TGFβ superfamily, and methods for screening for compounds useful in treating such conditions.

BACKGROUND OF THE INVENTION

The transforming growth factor beta (TGFβ) superfamily is a group of cytokines that regulate many aspects of cellular function. The structural prototype for the gene superfamily is TGFβ. TGFβ is produced as a precursor and the precursor structure is shared by most of the members of the TGFβ superfamily. The superfamily includes the TGFβ family, the inhibin family, the DPP/VG1 family and the Mullerian Inhibiting Substance Family.

The TGFβ family includes five members, termed TGFβ1 through TGFβ5, all of which form homodimers of about 25 kd (reviewed in Massague, 1990). The family also includes TGFβ1.2 which is a heterodimer containing a β1 and a β2 subunit linked by disulfide bonds. The five TGFβ genes are highly conserved over great evolutionary distances. The mature processed cytokines produced from the members of the gene family show almost 100% amino acid identity between species, and the five peptides as a group show about 60–80% identity.

All forms of TGFβ have been found to reversibly inhibit growth activity in normal, epithelial, endothelial, fibroblast, neuronal, lymphoid, and hematopoietic cell types (For review see Massague, 1990, Annu. Review Cell Biol. 6:597). In tissue culture, TGFβ has been shown to inhibit cell growth by blocking both cdk-4/cyclinD activation and cdk2/cyclinE activity, events required for G1 to S phase transition (M. E. Ewen, H. K. Sluss, L. L. Whitehouse, D. M. Livingston, Cell 74, 1009 (1993) and A. Koff, M. Ohtsuki, K. Polyak, J. M. Roberts, J. Massague, Science 260, 536 (1993)). The antiproliferative action of TGFβ has also been demonstrated in vivo (Silberstein and Daniel, 1987, Science 237:291–93; and Russell et al, 1988, Proc. Natl. Acad. Sci. U.S.A. 85:5126–30).

TGFβ can also stimulate cell proliferation although the effect may be secondary to other cellular responses. For example, TGFβ1 has been shown to promote the anchorage independent growth of normal rat kidney fibroblasts (Roberts et al., PNAS U.S.A. 78:5339, 1981; Roberts et al, Nature 295:417, 1982 and Twardzik et al., 1985, J. Cell. Biochem. 28:289, 1985) and it induces colony formation of AKR-2B fibroblasts (Tucker et al. Science 226:705, 1984). The inhibitory/stimulatory actions of TGFβ may depend on the cell type and the physiological state of the cells.

TGFβ is involved in mediation of cell adhesion. TGFβ action on normal mesenchymal, epithelial and lymphoid cells, and some tumor cell lines generally results in the up-regulation of cell adhesion. This up-regulation is mediated by enhanced synthesis and deposition of extracellular matrix components, decreased pericellular proteolysis, and modification of cell adhesion receptors (Massague, 1990).

Cellular differentiation processes of many cell lineages can be positively or negatively effected by TGFβ. TGFβ has been shown to exert positive effects on chondrocyte and osteogenic cell types (Massague, 1990).

The biological actions of TGFβ described above suggest a broad role for TGFβ in the physiologic setting. The ability of TGFβ to modulate DNA replication, cell differentiation, cell adhesion and extracellular matrix layout indicate a role for TGFβ in the generation and modification of signals that guide morphogenic events of embryogenesis. The activity of TGFβ as a promoter of extracellular matrix formation and a regulator of cell migration and development, is a major influence in inflammation and tissue repair processes. In fact, the administration of TGFβ1 into wound chambers or to incisional wounds has been shown to accelerate the wound healing response in general (Sporn et al., 1983, Science, 219:1329–31; Roberts et al., 1986, Proc. Natl. Acad. Sci. U.S.A. 83:4167–71; and Mustoe et al., 1987, Science 237:1333–36).

The TGFβ family of cytokines display an immunosuppressive activity in vitro and in vivo which is in part attributed to the antiproliferative action of TGFβ on lymphocytes (Kehrl et al 1986, J. Immunol. 137:3855), T-lymphocytes (Kehrl et al 1986, J. Exp. Med. 163:10371 and thymocytes (Ristow 1986, PNAS U.S.A. 83:5531). An excess of TGFβ activity in tissues may lead to an unbalanced deposition of extracellular matrix which may contribute to fibrosis, while a lack of TGFβ growth inhibitory activity may lead to oncogenic transformation.

Dis-regulation of TGFβ action has been implicated in the pathological processes of many diseases. TGFβ has been reported to be a pathogenic mediator in HIV infections and its associated diseases (Lotz, M. and Seth, P. Annals of the NY Acad. of Sciences 685:501, 1993).

TGFβ has also been implicated in the development of fibrosis including pulmonary fibrosis (Baecher-Allan and Barth, Regional Immunology 5(3–4):207, 1993), and fibrosis associated with chronic liver disease (Burt, A. D., J. of Pathology 170:105, 1993), hepatic veno-occlusive and idiopathic interstitial pneumonitis, which are major causes of morbidity and mortality after bone marrow transplantation (Anscher M. S. et al. N. Engl. J. Med. 328:1592, 1993), kidney disease (Border et al., Nature 369:360:361, 1992), and radiotherapy or radiation accidents (Martin M. et al Radiation Research 134:63, 1993). TGFβ2 has been found to be elevated in the eye of humans with proliferative vitreoretinopathy and in the skin in systemic sclerosis (Connor et al. J. Clin Invest. 83.:1661, 1989 and Kulozik et al., J. Clin. Invest. 86:917, 1990).

The use of TGFβ and TGFβ antagonists to modulate blood pressure is disclosed in PCT/US91/0449 published on Dec. 26, 1991. Recombinant TGFβ obtained from Chinese Hamster Ovary cells was reported to induce rapid, significant, and sustained decreases in arterial blood pressure of cynomolgus monkeys receiving daily injections of the recombinant molecule.

The DPP/VG1 family includes the bone marrow morphogenetic proteins (BMPs), termed BmP1 through SMRP, DPP and Vg1. The BMPs are osteoinductive agents present in adult bone. They are potent initiators of new bone formation and they appear to act on mesenchymal progenitor cells, directing their differentiation into both cartilage and bone-forming cells. It has also been suggested that they play an important role during embryonic skeleton formation (See Review by Rosen and Thies, in Trends in Genetics, 8(3)97, 1992 and references therein). Decapentaplegic (DPP) plays a fundamental role in dorsoventral body patterning and in imaginal disk formation in Drosophila (Padgett et al., 1987, Nature, 325:81–84). Vg1 is involved in embryonic development in *Xenopus laevis*.

The inhibin family includes the activins and inhibins. The activins are involved in the regulation of numerous biological processes. For example, they are involved in the proliferation of many tumor cell lines, the control of secretion and expression of the anterior pituitary hormones (EG, FSH, GH, and ACTH), neuron survival, hypothalamic oxytocin secretion, erythropoiesis, placental and gonadal steroidogenesis early embryonic development and the like. Inhibin molecules also help to regulate erythropoiesis and modulate the release of FSH (Mason et al., 1985, Nature 318:659–663 and Ling et al., Nature 321:779, 1986).

The Mullerian inhibiting substance family includes Mullerian inhibiting substance (MIS) which is an important morphogenetic signal in developing reproductive systems of mammalian embryos (Cate et al, Cell 45:685–698).

The members of the TGFβ superfamily may mediate signal transduction through families of related receptors. The cell surface receptors for TGFβ and activin are composed of type I and type II receptor chains, both of which contain a cysteine rich extracellular domain and a cytosolic serine/threonine protein kinase domain. The type I and type II receptors form heterodimers which appears to be necessary for cytokine-dependent intracellular signalling (Massague, Cell, 69:1067, 1992 and references therein, and Lin et al., Cell 68:775, 1992).

TGFβ binding proteins have been identified which do not function as signalling receptors. The proteoglycan betaglycan is the most widely distributed TGFβ binding protein after receptors I and II. Betaglycan is a membrane anchored proteoglycan that binds TGFβ via the core protein and it has been suggested that betaglycan acts as a receptor accessory molecule in the TGFβ systems (Massague, Cell, 69:1067, 1992 and references therein).

A number of other extracellular matrix proteins have been shown to bind TGF-β, including decorin, biglycan, thrombospondin and the serum glycoprotein α2-macroglobulin (Y. Yamaguchi, D. M. Mann, E. Ruoslahti, Nature 346, 281 (1990); S. Scholtz-Cherry J. E. Murphy-Ullrich, *J. Cell Biol.* 122, 923 (1993); O'Conner-McCourt, L., M. Wakefield *J. Biol. Chem.* 262, 14090 (1987); and J. Massague *Curr. Biol.* 1, 117 (1991)). Thrombospondin has been shown to bind and activate latent TGF-β, but does not neutralize cytokine activity. In contrast, decorin has been shown to neutralize the anti-proliferative activity of TGF-β (Yamaguchi et al., Nature 346:281, 1990). Decorin has also been found to antagonize the action of TGFβ in vivo using an experimental glomerulonephritis model (Border et al., Nature 360:361, 1992).

Bovine fetuin, is one of the first glycoproteins to be purified from fetal calf serum (FCS). Fetuin is analogous to human α-2 HS-glycoprotein (α2-HS) which is believed to be produced by the liver (Kellerman et al. J. Biol. Chem. 264:14121, 1989). Fetuin has been shown to promote cell growth in vitro without any known cell surface receptor (B. T. Puck, C. A. Waldren, C. Jones, Proc. Natl. Acad. Sci. U.S.A. 59, 192 (1968), and it has been shown to be a negative acute phase reactant (J. P. Lebreton, F. Joisel, J. P. Raoult, B. Lannuzel, J. P. Rogez, et al, J. Clin. Invest. 64, 118 (1979). M. Daveau, C. Davrinche, N. Djelassi, J. Lemetayer, N. Julen, et al, FEBS Lett. 273, 79 (1990)). Serum fetuin accumulates in bone (I. R. Dickson, A. R. Poole, A. Veis, Nature 256, 430 (1975), J. T. Triffitt, U. Gebauer, B. A. Ashton, M. E. Owen, Nature 262, 226 (1976), G. Rauth, O. Pöschke, E. Fink, M. Eulitz, S. Tippmer, et al, Eur. J. Biochem. 204, 523 (1992)) with highest concentrations found during bone growth. It also enhances bone resorption in cultured bone explants in vitro (G. C. Colclasure, W. S. Lloyd, M. Lamkin, W. Gonnerman, R. F. Troxler, et al, J. Clin. Endocrin. Metabolism 66, 187 (1988), and increases adipogenesis (A. J. Cayatte, L. Kumbla, M. T. R. Subbiah, J. Biol. Chem 265, 5883 (1990)). Inflammation is associated with significantly reduced serum fetuin concentrations (J. P. Lebreton, F. Joisel, J. P. Raoult, B. Lannuzel, J. P. Rogez, et al, J. Clin. Invest. 64, 118 (1979). M. Daveau, C. Davrinche, N. Djelassi, J. Lemetayer, N. Julen, et al, FEBS Lett. 273, 79 (1990)). Serum fetuin concentrations are also depressed in patients with Paget's disease, an affliction of increased bone turnover which leads to disordered and thickened bone (B. A. Ashton, R. Smith, Clin. Sci. 58, 435 (1980)). In a subset of osteogenesis imperfecta patients, the loss of bone is associated with elevated serum fetuin levels.

SUMMARY OF THE INVENTION

The present inventors have found that fetuin bound to and antagonized the antiproliferative activity of TGFβ, and it was able to inhibit the anti-proliferative activity of TGFβ in a dose dependent manner. The present inventors also demonstrated that the action of fetuin as an antagonist of TGFβ in tissue culture was due to binding of the two proteins. By using surface plasmon resonance which allows the visualisation of macromolecular interactions in real time, it was shown that fetuin could physically bind to TGFβ1. Fetuin was also found to bind to the closely related cytokine TGFβ2 with similar affinity. Fetuin also bound to immobilized BMP-2, BMP-4 and BMP-6. BMP-2 showed the highest affinity for fetuin.

Furthermore, the present inventors have significantly defined a binding domain common to fetuin and TGFβ receptor type II designated TGFβ Receptor II Homology (TRH1), which mediates their binding to cytokines of the TGFβ superfamily. The domain is defined by two disulphide loops which are designated a and b in FIGS. 6 to 8.

Other proteins such as bovine thyroglobulin were found to contain the TRH1 domain. Thyroglobulin was found to bind to the cytokines BMP-2, BMP-4, TGF-β1 and TGFβ2 with a higher affinity than fetuin. Thyroglobulin was also found to neutralize TGFβ1 activity in a growth inhibition assay.

The present inventors also found that ligand binding and ligand specificity was mediated by the TRH1b sequence within the TRH1 domain (See FIGS. 6 and 7 and the Sequence Listing SEQ. ID. NOS. 4 to 6). The TRH1 domain and the TRH1b subdomain have not been found in compounds which have previously been shown to bind to members of the TGFβ superfamily and neutralize their activity, for example, decorin.

The finding that fetuin and thyroglobulin complex with cytokines of the TGFβ superfamily through sequences within the TRH1 domain, and that they are antagonists of these cytokines, allows the identification of substances which modulate cytokines of the TGFβ superfamily, and which accordingly may be used in the treatment of conditions requiring modulation of TGFβ superfamily cytokines.

Therefore, the present invention relates to a method for assaying for the presence of a substance that modulates a cytokine of the TGFβ superfamily which comprises (a) reacting a substance which is suspected of modulating a cytokine of the TGFβ superfamily with a TGFβ binding compound which is not a TGFβ receptor and which contains a TRH1 domain, or a portion, or a mimetic thereof, and a cytokine of the TGFβ superfamily, under conditions where the TGFβ binding compound, portion, or mimetic thereof, and the cytokine are capable of forming a complex, the TGFβ binding compound, portion or mimetic thereof, and/or the cytokine being present in a known concentration, (b) assaying for complexes, free TGFβ binding compound, portion or mimetic thereof, and/or cytokine, and (c) comparing with a control.

The present invention further relates to the use of a TGFβ binding compound which is not a TGFβ receptor and which contains a TRH1 domain, for modulating cytokines of the TGFβ superfamily. In particular, the invention relates to the use of these compounds for the treatment of conditions requiring modulation of cytokines of the TGFβ superfamily. The compound may be introduced directly into an individual, or it may be produced Indirectly by expression of a gene encoding the TGFβ binding compound.

Therefore, the invention relates to a composition comprising at least one TGFβ binding compound which is not a TGFβ receptor and which contains a TRH1 domain, or a portion, or a mimetic thereof, and a pharmaceutically acceptable carrier, auxiliary or excipient. The composition may be used as an antagonist of TGFβ superfamily cytokines and therefore will be useful in the treatment of the above-mentioned conditions requiring modulation of TGFβ superfamily cytokines.

The invention also relates to a pharmaceutical composition comprising a recombinant molecule containing a gene encoding at least one TGFβ binding compound which is not a TGFβ receptor and which contains a TRH1 domain, or a portion, or a mimetic thereof.

The invention also contemplates a method of treating a subject suffering from a condition requiring modulation of cytokines of the TGFβ superfamily comprising administering an effective amount of a TGFβ binding compound which is not a TGFβ receptor and which contains a TRH1 domain, or a portion, or a mimetic thereof, or a substance identified by the methods of the invention.

The invention also contemplates a method of enhancing in an individual the activity of a growth factor whose effects are overridden by a cytokine of the TGFβ superfamily comprising administering to the individual a composition of the invention, or a substance which is an antagonist of cytokines of the TGFβ superfamily identified in accordance with the methods of the invention.

Still further the invention contemplates a method for assaying for a cytokine of the TGFβ superfamily in a sample comprising (a) reacting a sample suspected of containing the cytokine with a definite quantity of a TGFβ binding compound which is not a TGFβ receptor and which contains a TRH1 domain, or a portion, or a mimetic thereof, and a definite quantity of the cytokine, under conditions where the compound and the cytokine are capable of forming a complex, the compound and/or the cytokine being present in a known concentration, (b) assaying for complexes, free compound and/or cytokine, and (c) comparing with a control.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will now be described in relation to the drawings in which:

FIG. 6 is a multiple alignment of fetuin sequences from bovine, pig, sheep, rat and human (SEQ. ID. NO. 8, 9, 10, 11, and 12, respectively);

FIG. 8 is an alignment of the fetuin, bthyroglobulin, hTGF-betaRII, and mTGF-betaRI sequences (SEQ. ID. NO. 2, 4, 3, and 13, respectively);

FIG. 11 shows the sequence of the TGFβ type II receptor.

DETAILED DESCRIPTION OF THE INVENTION

As hereinbefore mentioned, the present invention relates to a method for assaying for the presence of a substance that modulates cytokines of the TGFβ superfamily. A substance which is suspected of modulating cytokines of the TGFβ superfamily is reacted with a TGFβ binding compound which is not a TGFβ receptor and which contains a TRH1 domain, or a portion, or a mimetic thereof, and a cytokine of the TGFβ superfamily. Suitable reaction conditions are employed to permit formation of a complex between the compound and the cytokine. The compound and/or the cytokine are present in a known concentration. The complexes, free compound and/or cytokine are assayed and the results are compared with a control.

"Cytokines of the TGFβ superfamily", "Members of the superfamily of TGFβ of cytokines", or "TGFβ superfamily cytokines" referred to herein includes cytokines having the structural characteristics of the members of the TGFβ superfamily. The structural prototype for the gene superfamily is TGFβ. TGFβ is produced as a precursor which is characterised by having an N-terminal hydrophobic signal sequence for translocation across the endoplasmic reticulum, a pro-region, and a C-terminal bioactive domain. Prior to release from the cell, the pro-region is cleaved at a site containing four basic amino acids immediately preceding the bioactive domain (Massague, 1990).

Figure 2:
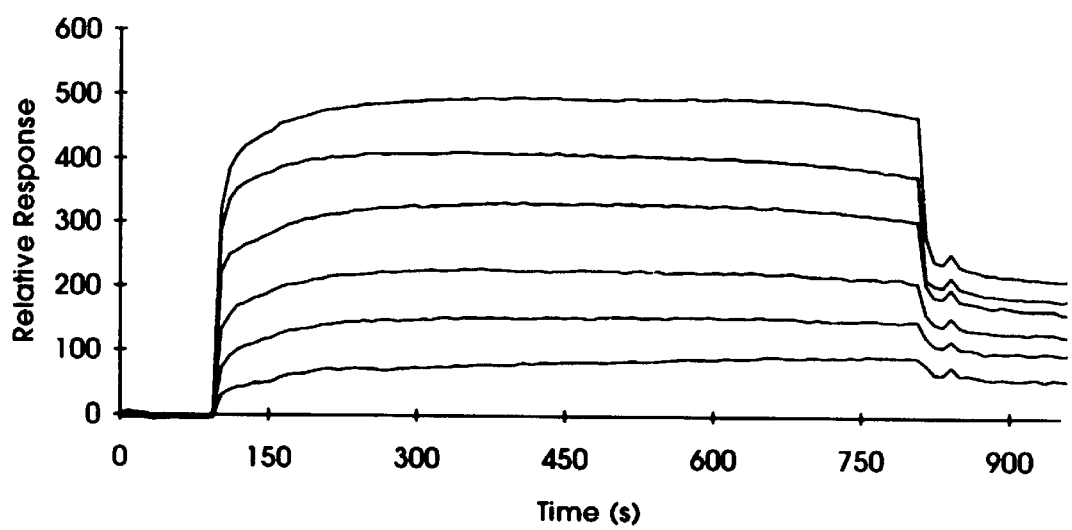
FIG. 2 is a sensorgram overlay plot showing bovine fetuin binding in response units (R.U.) to immobilized TGF-β1 (A)

The precursor structure of TGFβ is shared by members of the TGFβ superfamily, with the exception of the TGFβ4 precursor which lacks a distinguishable signal sequence. The degree of identity between family members in the C-terminal bioactive domain is from 25 to 90% (See Basler et al. Cell, 73:687, 1993, FIG. 2). At least 7 cysteines are conserved in the bioactive domain in all members of the superfamily and all nine cysteines are conserved in the TGFβ family and the inhibin β chains. With the exception of Mullerian Inhibiting Substance (MIS) (Cate et al., 1986), the bioactive domain is cleaved to generate a mature monomer.

Examples of cytokines of the TGFβ superfamily include the cytokines of the TGFβ family, the inhibin family, the DPP/VG1 family and the Mullerian Inhibiting Substance Family.

The TGFβ family includes five members, termed TGF1 through TGFβ5, all of which form homodimers of about 25 kd (reviewed in Massague, 1990). The family also includes TGFβ1.2 which is a heterodimer containing a β1 and a β2 submit linked by disulfide bonds. The five TGFβ genes are highly conserved over great evolutionary distances. The mature processed cytokines produced from the members of the gene family show almost 100% amino acid identity between species, and the five peptides as a group show about 60–80% identity.

The DPP/VGI family includes the six BMPs termed BMP-2 through BMP-7, Vg1, and DPP. BMPs are 30–40% homologous to members of the TGFβ family. BMP2–7 share considerable homology with members of the Inhibin family which includes the inhibins/activins. The inhibins are composed of an α subunit, and either a βA subunit (inhibin A), or a βB subunit (inhibin B). The amino acid identity of the two β subunits is about 60% while the α subunit sequence is very divergent (about 25% identity). The family includes inhibin A (α.βA dimer), inhibin B (α.βB dimer), activin A (βA homodimer), and activin AB (βA.βB dimer) (Massague, 1990).

The Mullerian Inhibiting Substance Family includes the Mullerian Inhibiting Substance (MIS) homodimer. The deduced sequence of the MIS C-terminal domain is about 25% identical to that of the other members of the superfamily. MIS is a disulfide-linked homodimer of 70–74 kd glycosylated chains that contains the glycosylated N-terminal extension uncleaved from the C-terminal domain (Massague, 1990).

Preferably, the methods and compositions described herein incorporate members of the TGFβ family and the DPP/VG1 family, most preferably TGFβ1, TGFβ2, BMP-2, BMP-4 and BMP-6.

Cytokines of the TGFβ superfamily can be isolated from natural or recombinant sources. For example, TGFβ1 may be synthesized by a variety of normal and transformed cells in culture (Roberts et al., 1981, Proc. Natl. Acad. Sci. U.S.A. 78:5339–5343) and it has been purified from placenta (Frolik et al., 1983, Proc. Natl;. Acad. Sci. U.S.A. 80:3676–3680), kidney (Roberts et al., 1983, Biochemistry 22:5692–5698), urine (Twardzik et al., 1985, J. Cell. Biochem. 28:289–297) and blood platelets (Childs et al., 1982, Proc. Natl;. Acad. Sci. U.S.A. 79:5312–5316). BMP-2,-3, 6 and 7 may be isolated from human and/or bovine bone.

Large quantities of the cytokines may be obtained by recombinant techniques using host cells transfected with recombinant vectors containing the coding sequence for the cytokine. The cytokines may also be obtained from commercial sources. (For example, TGFβ1 may be obtained from Collaborative Research, Bedford, Mass.).

The TGFβ binding compound used in the methods and compositions described herein may be a glycoprotein or polypeptide. The compound binds to a cytokine of the TGFβ superfamily, preferably TGFβ1, with a $K_D$ of greater than $10^{-5}$ and/or neutralizes the activity of a TGFβ cytokine such as TGFβ1 or BMP-2 in a growth inhibition assay as described herein. The TGFβ binding compound is not a natural target TGFβ receptor namely a type I or type II receptor of TGFβ or activin which contain a cytosolic serine/threonine protein kinase domain. The sequence of the TGFβ type II receptor is set out in FIG. 11 and in the Sequence Listing as SEQ. ID. NO. 1.

The protein portion of the TGFβ binding compound contains at least one amino acid sequence of the TRH1 domain, or a portion or a mimetic thereof. The TRH1 domain comprises a region about 43 amino acids in length, containing two disulfide loops designated a and b in FIGS. 7 and 8. A TRH1 domain may be identified using the GCG routine "findPatterns" and the following pattern: Cx{8,14}(N,Q)X{12,16}CX{4,5}(K,R)X{2,6}(S,T)X{4,9}CX{0,2}DX{5,6}(D,E) (See Example 3 herein). The TRH1 domain from fetuin is shown in the Sequence Listing as SEQ. ID. NO. 2 and in FIG. 8; the TRH1 domain from the TGFβ type II receptor is shown in the Sequence Listing as SEQ. ID. NO. 3 and in FIG. 8; and, the TRH1 domain from thyroglobulin is shown in the Sequence Listing as SEQ. ID. No. 4 and in FIG. 8. Preferably, the compound contains a portion of the TRH1 domain having the amino acid sequence of the TRH1b subdomain which contains about 20 amino acids. A TRH1b subdomain may be identified using the GCG routine "findPatterns" and the following pattern: CX{4,5}(K,R)X{2,6}(S,T)X{4,9}CX{0,2}DX{5,6}(D,E). The TRH1b subdomain from fetuin, the TGFβ type II receptor, and thyroglobulin are shown in the Sequence Listing as SEQ. ID. NOS. 5, 6, and 7, respectively.

Examples of TGFβ binding compounds which may be used in the methods and compositions of the invention are fetuin, including human fetuin also known as α-$_2$-HS glycoprotein, thyroglobulin, and kininogens (Kellerman et al. Biochem. J. 247:15, 1987).

The protein portion of the TGFβ binding compound may include sequences which are homologous to the amino acid sequence of the TRH1 domain, or a portion thereof. A sequence which is homologous to the TRH1 domain or a portion thereof such as the TRH1b subdomain is defined as a sequence which has at least about 40% and 70% identity, respectively. A TGFβ binding compound containing a homologous sequence should be capable of binding to a TGFβ cytokine, preferably TGFβ1, with a $K_D$ of greater than $10^{-5}$ and/or neutralizing activity of a TGFβ cytokine such as TGFβ1 or BMP-2 in a growth inhibition assay as described herein.

It will be appreciated that a TGFβ binding compound may be modified by substituting amino acids for like amino acids. For example, a basic amino acid may be substituted with a different basic amino acid, or a hydrophobic amino acid may be substituted with a different hydrophobic amino acid in the TRH1 domain or TRH1b subdomain.

Mimetics of the TGFβ binding compounds may also be used in the methods and compositions of the invention. The term "mimetic" refers to compounds which have a related three dimensional structure i.e. compounds which have one or both of the characteristic disulfide loop structures as shown schematically in FIG. 7, preferably the loop structure designated "b". The selection of mimetics may be done using methods such as described in for example P. S. Farmer, in Drug Design, E. J. Ariens, Ed. (Academic Press, New York, 1980) Vol. 10, p.119–143; Ball J. B., P. F. Alewood, J. Mol. Recognition 3,55, 1990; B. A. Morgan and J. A. Gainer, Annu. Rep. Med. Chem. 24, 243, 1989; and R. M. Friedinger, Trends Pharmacol. Sci. 10, 270 1989.

A TGFβ binding compound may also be a chimeric molecule. For example, the TRH1b region of fetuin (SEQ.

ID. NO. 5 and Cys 114 to Cys 132 in SEQ. ID. NO. 2) can be replaced by the corresponding loop from the TGFβ type II receptor (SEQ. ID. NO. 6 and Cys 84 to Cys 101 in SEQ. ID. NO. 3).

TGFβ binding compounds such as fetuin and thyroglobulin may be obtained using conventional isolation and purification techniques. For example, the compounds may be obtained by ammonium sulfate fractionation of fetal calf serum followed by gel filtration chromatography. They may also be obtained from commercial sources (e.g. Sigma, St. Louis, Mo., U.S.A.). TGFβ binding compounds may also be synthetically constructed using conventional methods such as chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of organic Chemistry, ed. E. Wansch, Vol. 15 I and II, Thieme, Stuttgart).

A TGFβ binding compound may also be expressed in a host cell including bacteria, yeast, insect or mammalian cells using methods well known in the art (see, for e.g., Itakura et al., U.S. Pat. No. 4,704,362; Hinnen et al., PNAS U.S.A. 75:1929–1933, 1978; Murray et al., U.S. Pat. No. 4,801,542; Upshall et al., U.S. Pat. No. 4,935,349; Hagen et al., U.S. Pat. No. 4,784,950; Axel et al., U.S. Pat. No. 4,399,216; Goeddel et al., U.S. Pat. No. 4,766,075; and Sambrook et al. Molecular Cloning A Laboratory Manual, 2nd edition, Cold Spring Harbor Laboratory Press, 1989).

Preferably, the expression system is a mammalian expression system. For example, Chinese Hamster Ovary (CHO) cells may be used to produce a correctly folded and glycosylated fetuin, and to permit recovery of the protein from serum-free cell culture supernatants. Both a transient and stable approach may be used. The former approach may be based on the SFU virus replicon which can be used to quickly produce relatively large amounts of recombinant protein. The stable approach may employ the well characterized cytomegalovirus (CMV) promoter which allows for a more permanent and constant source of the protein. The coding region of a cDNA encoding the protein can be cloned out of a cDNA library using the polymerase chain reaction (PCR) amplification techniques (Mullis el al., U.S. Pat. No. 4,863,195 and Mullis, U.S. Pat. No. 4,683,202). The nucleotide sequence may be confirmed by DNA sequencing. A PCR based cloning strategy will allow introduction of convenient restriction sites for subcloning into the expression vectors.

It will be appreciated that the selection of the TGFβ binding compound and the TGFβ superfamily cytokine in the method of the invention will depend on the nature of the substance to be assayed. It will also be appreciated that the selection of the compound and TGFβ superfamily cytokine in the method of the invention will allow for the identification of a specific substance that affects a specific interaction. Thus, the identification of the specific site of binding of the TRH1 domain to TGFβ superfamily cytokines by the present inventors allows the identification of specific substances that modulate TGFβ superfamily cytokines.

Conditions which permit the formation of cytokine-TGFβ binding compound complexes may be selected having regard to factors such as the nature and amounts of the cytokine and the TGFβ binding protein.

The complexes, and free compounds and cytokines in the methods of the invention may be isolated by conventional isolation techniques, for example, salting out, chromatography, electrophoresis, gel filtration, fractionation, absorption, polyacrylamide gel electrophoresis, agglutination, or combinations thereof.

The complexes or free compounds or cytokines may be assayed using known methods. To facilitate the assay of the components, antibody against the compound or cytokine which may be labelled, or a labelled compound or cytokine may be utilized. The components may also be assayed by determining the ability to neutralize activity of a TGFβ cytokine such as TGFβ1 or BMP-2 in a growth inhibition assay as described herein.

The TGFβ binding compounds and TGFβ superfamily cytokines may be used to prepare antibodies and the antibodies may be used to facilitate isolation and separation of complexes and free compound, or cytokine. As described below, antibodies to the TRH1 domain and portions thereof may also be used to neutralize the activity of a TGFβ cytokine by blocking its binding to its native receptor, and accordingly they may allow therapeutic intervention in cases where there is excessive TGFβ cytokine activity such as cases of fibrosis, or where TGFβ serves as an autocrine growth factor for tumors. They may also be used for assaying for the presence of a TGFβ superfamily cytokine in a biological sample in specific diagnostic applications.

Within the context of the present invention, antibodies are understood to include monoclonal antibodies, polyclonal antibodies, antibody fragments (e.g., Fab, and $F(ab')_2$ and recombinantly produced binding partners. Polyclonal antibodies may be readily generated by one of ordinary skill in the art from a variety of warm-blooded animals such as horses, cows, various fowl, rabbits, mice, or rats. Monoclonal antibodies may also be readily generated using conventional techniques (see U.S. Pat. Nos. RE 32,011, 4,902,614, 4,543,439, and 4,411,993 which are incorporated herein by reference; see also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Binding partners may also be constructed utilizing recombinant DNA techniques to incorporate the variable regions of a gene which encodes a specifically binding antibody (See Bird et al., Science 242:423–426, 1988).

Antibodies specific for some of the cytokines may also be obtained from commercial sources. For example, antibodies to cytokines of the TGFβ family may be obtained from American Diagnostics Inc., Connecticut U.S.A., Oncogene Science, NY, U.S.A., and Dimension Laboratories, Mississauga, Canada.

The antibodies against the compound or cytokines may be labelled using conventional methods with various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive phosphorous $^{32}P$, iodine $I^{125}$, $I^{131}$ or tritium. Antibodies specific for the compound or cytokine may also be coupled to electron dense substances, such as ferritin or colloidal gold, which are readily visualised by electron microscopy.

The TGFβ binding compound or cytokine used in the method of the invention may be insolubilized. For example, they may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinylether-maleic acid copolymer, amino acid copolymer, ethylene-maleic acid copolymer, nylon, silk, etc. The carrier may be in the shape of, for example, a tube, test plate, beads, disc, sphere etc.

The insolubilized compound or cytokine may be prepared by reacting the material with a suitable insoluble carrier using known chemical or physical methods, for example, cyanogen bromide coupling.

The methods of the invention may be used to assay for a substance that modulates TGFβ superfamily cytokines preferably a suspected agonist or antagonist. Generally an antagonist may constitute any molecule with similar binding activity to a TGFβ superfamily cytokine but incapable of propagating the biological response normally induced by the cytokine. An antagonist may also be a molecule that mimics the binding site on the receptor for the cytokine. For example, an antagonist constitutes a molecule containing the TRH1 domain. As described in detail herein compounds such as fetuin and thyroglobulin which contain the TRH1 domain are antagonists of cytokines of the TGFβ superfamily. On the other hand, an agonist constitutes a molecule which binds to the specific binding site on the receptor for the cytokine i.e. the TRH1 domain, in some advantageous manner compared to the natural cytokine. The agonist or antagonist may be an endogenous physiological substance or it may be a natural or synthetic drug.

The invention also relates to a pharmaceutical composition comprising at least one TGFβ binding compound. The pharmaceutical compositions may also contain substances identified using the methods described herein. The pharmaceutical compositions may be used as an agonist or antagonist of the interaction of a TGFβ cytokine and a TβRII. The composition preferably contains fetuin, more preferably human fetuin, also known as α-2 HS-glycoprotein. Fetuin is particularly suitable as a pharmacological agent since it is a natural human compound which is non-immunogenic, and it can be produced as a recombinant molecule as described herein.

The pharmaceutical compositions of the invention contain at least one TGFβ binding compound, alone or together with other active substances. Such pharmaceutical compositions can be for oral, topical, rectal, parenteral, local, inhalant or intracerebral use. They are therefore in solid or semisolid form, for example pills, tablets, creams, gelatin capsules, capsules, suppositories, soft gelatin capsules, gels, membranes, tubelets. The compositions of the invention may also be conjugated to transport molecules such as transferrin to facilitate transport of the composition across the blood brain barrier.

The pharmaceutical composition of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can he administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., U.S.A. 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids.

The invention also relates to a composition comprising a recombinant molecule containing a gene encoding at least one TGFβ binding compound which is not a TGFβ receptor and which contains the TRH1 domain, or a portion, or a mimetic thereof. The recombinant molecule also contains suitable transcriptional or translational regulatory elements. Suitable regulatory elements may be derived from a variety of sources, and they may be readily selected by one of ordinary skill in the art. Examples of regulatory elements include: a transcriptional promoter and enhancer or RNA polymerase binding sequence, a ribosomal binding sequence, including a translation initiation signal. Additionally, depending on the vector employed, other genetic elements, such as selectable markers, may be incorporated into the recombinant molecule. The recombinant molecule may be introduced into cells of a subject using in vitro delivery vehicles such as retroviral vectors, adenoviral vectors and DNA virus vectors. They may also be introduced into such cells in vivo using physical techniques such as microinjection and electroporation or chemical methods such as coprecipitation and incorporation of DNA into liposomes. The compositions may also be delivered in the form of an aerosol or by lavage.

The present invention also provides for methods in which a patient suffering from a condition requiring modulation of cytokines of the TGFβ superfamily is treated with an effective amount of a TGFβ binding compound. Therapeutic methods comprising administering agonists or antagonists identified with the methods of the present invention are also within the scope of the present invention.

The TGFβ binding compounds, substances identified using the method of the invention, antibodies, and compositions containing same, may be used in a variety of applications. Since the TGFβ cytokines are involved in many biological processes, the compounds, substances, antibodies and compositions can be applied to the modulation of these processes.

Agonists of cytokines of the TGFβ family identified using the method of the invention may be used to stimulate wound healing, to suppress the growth of TGFβ sensitive tumors, to suppress the immune response, and to stimulate angiogenesis. The immune response may be suppressed in transplant cases to reduce the rejection of the transplanted organ.

Antagonists of cytokines of the TGFβ family can be used to block the binding of an endogenous TGFβ to its natural target receptors thereby blocking cell proliferative or inhibitory signals generated by the ligand-receptor binding event. Antagonists such as TGFβ binding compounds and antibodies would thereby stimulate immune responses and reduce the deposition of extracellular matrix. Accordingly, antagonists would be particularly suitable for the treatment of conditions such as fibrosis including pulmonary fibrosis, fibrosis associated with chronic liver disease, hepatic veno-occlusive and idiopathic interstitial pneumonitis, kidney disease, and radiotherapy or radiation accidents; proliferative vitreoretinopathy; systemic sclerosis; autoimmune disorders such as rheumatoid arthritis, Graves disease, systemic lupus erythematosus, Wegener's granulomatosis, sarcoidosis, polyarthritis, pemphigus, pemphigoid, erythema multiforme, Sjogren's syndrome, inflammatory bowel disease, multiple sclerosis, myasthenia gravis keratitis, scleritis, Type I diabetes, insulin-dependent diabetes mellitus, Lupus Nephritis, and allergic encephalomyelitis; proliferative disorders including various forms of cancer such as leukemias, lymphomas (Hodgkins and non-Hodgkins), sarcomas, melanomas, adenomas, carcinomas of solid tissue, hypoxic tumors, squamous cell carcinomas of the mouth, throat, larynx, and lung, genitourinary cancers such as cervical and bladder cancer, hematopoietic cancers, head and neck cancers, and nervous system cancers, benign lesions such as papillomas, arthrosclerosis, angiogenesis, and viral infections, in particular HIV infections.

Antagonists of cytokines of the TGFβ family may also be used to elevate blood pressure through the inhibition of hypotension induced by TGFβ. Methods which lower and/or maintain the level of circulating TGFβ in a subject may result in a similar pressor effect and may prevent excessive hypotensive signal generation and resulting hypotension.

The stimulation of FSH release by activin can be enhanced by the administration of a specific TGFβ binding compound. The compound would prevent the formation of a complex between activin and its natural receptor which would then act to stimulate the release of FSH. Therefore, the TGFβ binding compound would reduce the effect of activin by blocking the normal interaction between activin and activin receptor. Accordingly, the TGFβ binding compound can be applied to the control of fertility in humans, domesticated animals, and animals of commercial interest. The action of activin on erythropoiesis can also be modulated by administering a modulating effective amount of a TGFβ binding compound. The compounds, substances, antibodies and compositions of the invention can also be used in the diagnosis and/or treatment of activin-dependent tumors or for enhancing the survival of brain neurons.

As another example, agonists of receptors of the DPP/VG1 family, in particular BMP-2 to BMP-7, identified using the method of the invention may be used to induce bone formation, and in particular they can be used to repair fractures.

The utility of the compounds, antibodies, and compositions of the invention may be confirmed in animal experimental model systems. For example, therapeutic utility in fibrotic conditions may be tested by examining the susceptibility of mice to the induction of pulmonary fibrosis by bleomucin sulfate (Baecher-Allan, Regional Immunology 5(3–4):207, 1993). The well-characterized pig model of radiation induced fibrosis described in Martin et al, Radiation Research 134(1)63, 1993, and the experimental glomerulonephritis model described in Border et al, Nature 360:361, 1992 may also be utilised. Other models which may be useful in confirming the utility of the compounds, substances and compositions of the present invention include those for wound healing (e.g. the fetal tissue repair model described in Bleacher et al. Dermatologic Clinics 11(4):677, 1993), bone repair (e.g. bone induction in rats—Yasko, A. W., et al., Orthop. Trans. 15:501, 1991; sheep femur—Gerhart T. N. et al, Trans. 37 Annual Meeting Orthop. Res. Soc, Anaheim C. A. Catherson, B., ed) 16(1), p.172, 1991; and dog mandible—Toriumi D. M. et al, Archiv. Otolarynogol. Head Neck Surg. 117:1101–1112, 1991), and autoimmune diseases (e.g. MRL-1pr/ipr mice are a model for systemic lupus erythematosus, and NZBxN-ZWf1 mice which demonstrate clinical symptoms comparable to those found with human autoimmune diseases—Theofilopoulos and Dixon, Adv. Immunol. 37, 1985).

It would also be apparent to one skilled in the art that the above described methods, compounds, substances, antibodies, and compositions may be used to study the cytokines of the TGFβ superfamily and, accordingly, will provide further insight into the role of the cytokines in growth, differentiation and morphogenesis.

Cytokines of the TGFβ family arrest the growth of cells thereby overriding the action of other growth factors such as EGF, bFGF, IL-1α, IL-1β, Int-2, keratinocyte growth factor, IL-2, GM-CSF, G-CSF, CNTF, EGF, TGFα, human growth hormone, NGF, PDGF, insulin, IGF-1, IGF-2, bombyxin, glial growth factor TNF, and CD40 ligand (Ewen et al., Cell 74:1009, 1993). For effective use of growth factors in a clinical setting, it would be desirable to reduce the activity of TGFβ cytokines concomitantly.

Accordingly, the invention also contemplates a composition comprising a TGFβ binding compound in combination with a growth factor whose effects are overridden by a cytokine of the TGFβ superfamily. The invention also relates to a method of enhancing treatment of an individual with a growth factor whose effects are overridden by a cytokine of the TGFβ superfamily comprising concomitantly administering with the growth factor a TGFβ binding compound which is not a receptor of TGFβ cytokine and which contains a TRH1 domain. Other antagonists of the binding of cytokines of the TGFβ superfamily identified using the methods of the invention may also be used in these compositions and methods to enhance the activity of growth factors.

Another application of the present invention is the assay of samples for the presence or absence of members of the TGFβ superfamily of cytokines. For example, serum from a patient displaying symptoms related to pathways mediated by members of the superfamily of TGFβ cytokines can be assayed to determine if the observed symptoms are perhaps caused by over-or under-production of such a cytokine. The assays can be carried out in a variety of ways as can readily be identified by one of skill in the art. For example, competitive assays can be employed as well as immunological assays using antibodies of the invention such as radioimmunoassays, ELISA, ERMA, and the like.

In an embodiment of the invention a competitive binding assay is provided for assaying for a cytokine of the TGFβ superfamily in a sample comprising (a) reacting a sample suspected of containing the cytokine with a definite quantity of a TGFβ binding compound which is not a TGFβ receptor and which contains a TRH1 domain or a portion, or a mimetic thereof, and a definite quantity of the cytokine, under conditions where the compound and the cytokine are capable of forming a complex, the compound and/or the cytokine being present in a known concentration, (b) assaying for complexes, free compound and/or cytokine, and (c) comparing with a control.

The method may be used to assay for TGFβ cytokines in tissues and biological samples for example clinical samples of blood, blood product, serum, body fluids, secretions, faeces, washings such as throat washings, tissue homogenates and cell culture fluids containing or suspected of containing the cytokines. The cytokines and TGFβ binding compounds which may be used in the method are described in detail above with reference to the method for assaying for substances affecting TGFβ cytokines. Conditions which permit the formation of cytokine-TGFβ binding compound complexes may be selected having regard to factors such as the nature and amounts of the cytokine and the TGFβ binding protein.

The following non-limiting examples are illustrative of the present invention;

EXAMPLES

Example 1

The ability of fetuin and thyroglobulin to bind to and antagonize TGFβ was tested. $^3$H-Thymidine incorporation in Mv1Lu cells was assessed in the presence of TGF-β1 (12 pM) alone, and with increasing concentrations of bovine fetuin (closed circles in FIG. 1); bovine thyroglobulin (open triangles in FIG. 1); or bovine serum albumin (closed triangles in FIG. 1).

Figure 1:
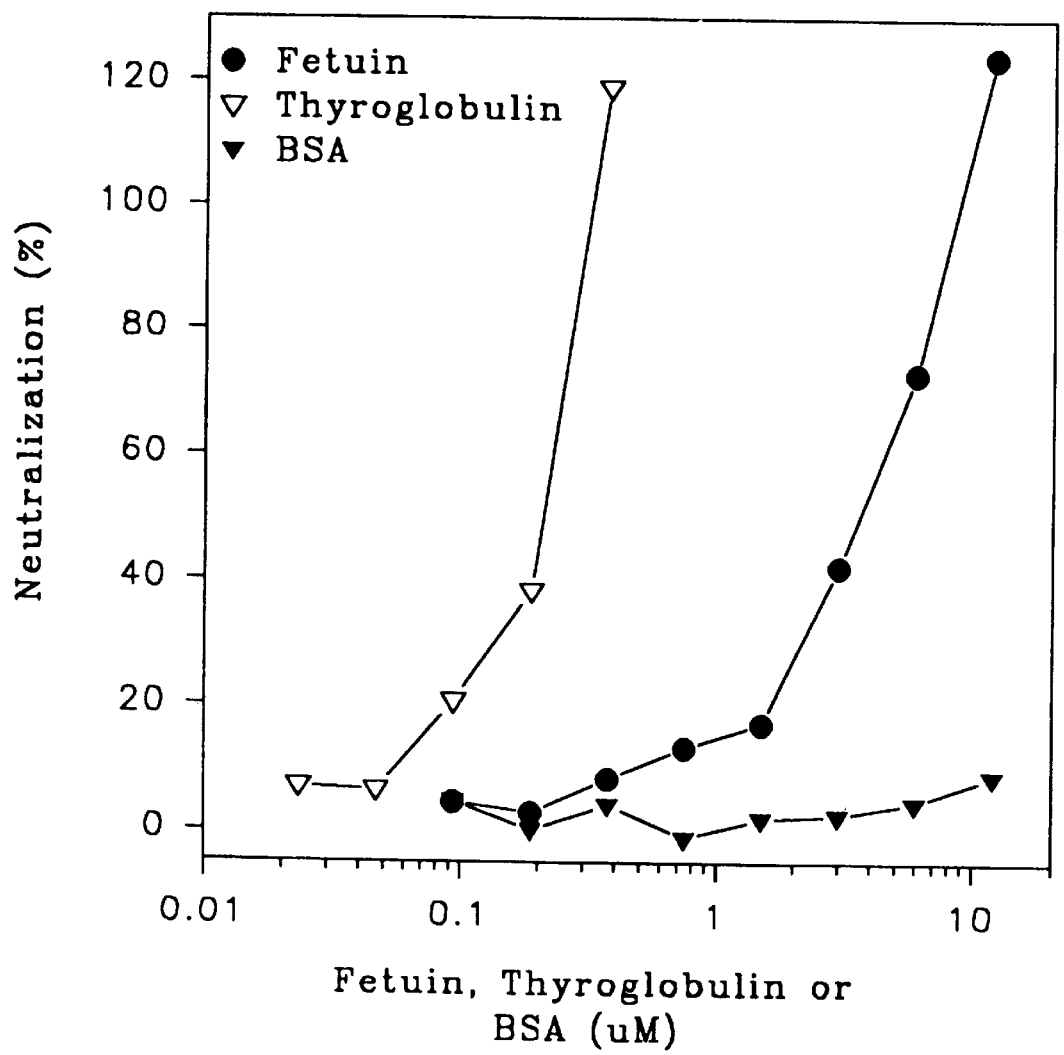
FIG. 1 is a graph showing that bovine fetuin and bovine thyroglobulin neutralize the antiproliferative activity of TGFβ on cultures of Mv1Lu cells.

Mv1Lu cells were seeded at 20,000 cells/well in a 96 well plate containing 0.2% FCS in α-MEM and incubated with the indicated concentrations of proteins for 18 hr. The cells were then pulsed with 8 μCi/ml methyl-$^3$H-thymidine (NEN, Boston, Mass. for 6 hr. Cells were trypsinized, harvested onto filtermats and counted in a β-Counter. Percent neutralization is defined as incorporation in the presence of 12 pM TGF-β1 alone set at 0%, and incorporation without additions as 100%. The difference in $^3$H-thymidine incorporation between 0% and 100% was 7.5 fold. Each point in FIG. 1 represents the mean of duplicate determinations, and the results are representative of three experiments. Bovine thyroglobulin and bovine fetuin (obtained by ammonium sulfate fractionation of FCS, followed by gel filtration chromatography) were purchased from Sigma (St. Louis, Mo.), BSA (fraction V) from Boehringer Mannheim (Laval, Quebec), and TGF-β1 (purified human) from Collaborative Research (Bedford, Mass.). Before use, bovine thyroglobulin was spun twice in a centricon (M.W. cutoff of 10,000 Da) micro-concentrator (Amicon, Beverly, Mass.) to remove any excess Iodine and T3/T4 thyroid hormones.

FIG. 1 shows that bovine fetuin and bovine thyroglobulin neutralize the antiproliferative activity of TGF-β1 on cultures of Mv1Lu cells. Maximal effect for both fetuin and thyroglobulin was approximately 150% neutralization, suggesting that endogenous TGF-β in the cultures is also inhibited resulting in a net stimulation of cell growth compared to controls. Similar observations have been reported for the TGF-β antagonist decorin (Y. Yamaguchi, D. M. Mann, E. Ruoslahti, Nature 346, 281 (1990). S. Scholtz-Cherry J. E. Murphy-Ullrich, J. Cell Biol. 122, 923 (1993); O'Conner-McCourt, L., M. Wakefield J. Biol. Chem. 262, 14090 (1987); and, J. Massague Curr. Biol. 1, 117 (1991)).

Fetuin was able to inhibit the anti-proliferative activity of TGF-β1 on Mv1Lu cells in a dose dependent manner, with half-maximal inhibition (IC$_{50}$) at 4.2×10$^{-6}$M. Thyroglobulin also neutralized TGF-β1 activity in the Mv1Lu growth inhibition assay with an IC$_{50}$=2.2×10$^{-7}$M (FIG. 1). The IC$_{50}$ for inhibition of TGF-β1 activity by thyroglobulin was 20 fold lower than for fetuin, a difference that is also reflected in the K$_D$ values for association of TGF-β with these glycoproteins (Table 1)

Example 2

To determine whether the action of fetuin and as an antagonist of TGF-β1 in tissue culture was due to direct binding of the two proteins, their interaction by surface plasmon resonance using BIAcore (Pharmacia Biosensor, Piscataway, N.J.) (M. Malmqvist, Nature 361, 186 (1993) and S. C. Schuster, R. V. Swanson, L. A. Alex, R. B. Bourret, M. I. Simon, Nature 365, 343 (1993)) was examined. In this system, a purified protein serving as the ligand is covalently coupled to a carboxymethylated dextran surface, and binding molecules (ie. the analyte) are passed in a fluid phase across the surface. Binding of the analyte to ligand causes a change in reflected light which is directly proportional to mass bound, and is measured in arbitrary response units (R.U.). Analyte-ligand binding is observed as both increasing response with time during the injection of analyte, and the difference in the position of the baseline before and after injection.

More particularly, purified human TGF-β1 (Collaborative Research, Bedford, Mass.) and recombinant human BMP-2 (a gift of Genetics Institute, Cambridge, Mass.) were immobilized onto the carboxy-methylated dextran surface of the CM5 sensor chip as described in M. Malmgvist, Nature 361, 186 (1993) and S. C. Schuster, R. V. Swanson, L. A. Alex, R. B. Bourret, M. I. Simon, Nature 365, 343 (1993). 1000 R.U. equals approximately 1 ng/mm$^2$. The running buffer was 20 mM Hepes (pH7.2), 150 mM NaCl and the flow rate for all sensorgrams was 3 μl/min. Injection volumes were 36 μl for FIG. 2, 4 and 5 and 45 μl for FIG. 3. Regeneration of the surface to remove bound analyte was done by injecting 10 μl of 1M glucose-6-phosphate, or 1 μl of 20 mM NaOH for TGF-β1 and BMP-2 coated-surfaces, respectively. Protein concentrations in each experiment were (FIGS. 2 and 3), 2, 5, 10, 20, 30, 40 μM; (FIG. 4), 0.21, 0.31, 0.41, 0.62, 0.82, 1.24 μM; (FIG. 5), 0.22, 0.29, 0.44, 0.59, 0.88 μM. R.U. for the immobilized cytokine in each experiment was 2850 R.U. for FIGS. 2 and 3; 7450 R.U. for FIG. 4, and 5300 R.U., for FIG. 5 respectively.

Figure 3:
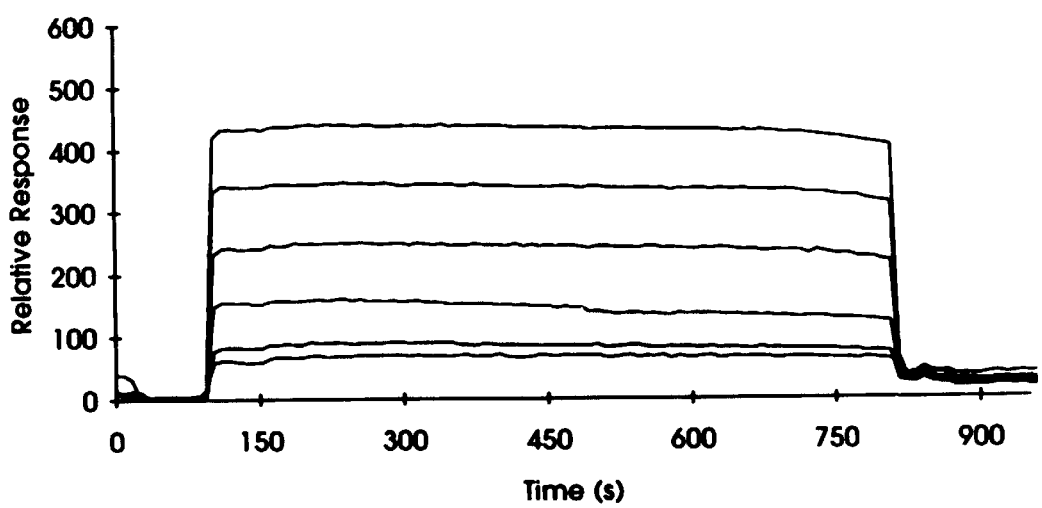
FIG. 3 is a sensorgram overlay plot of the non-binding control human transferrin.
Figure 4:
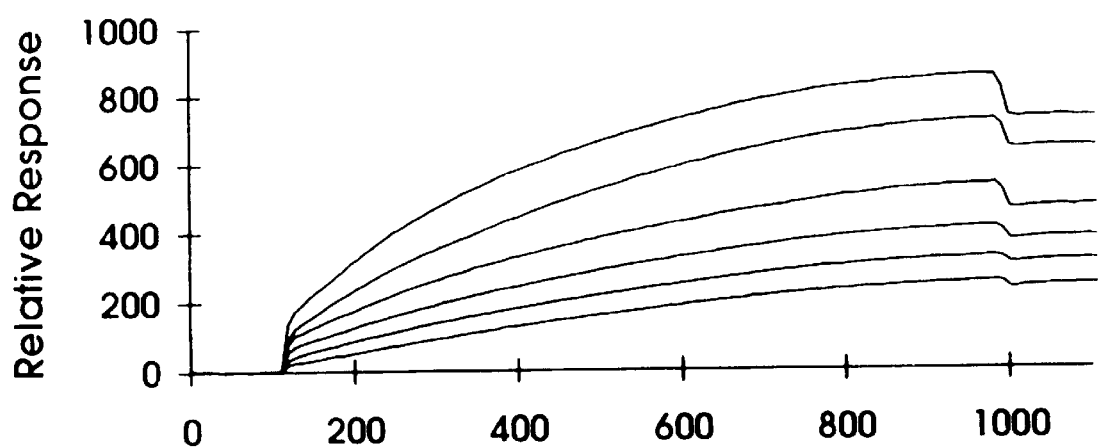
FIG. 4 is a sensorgram overlay plot showing bovine fetuin binding in response units (R.U.) to immobilized BMP-2 (C)
Figure 5:
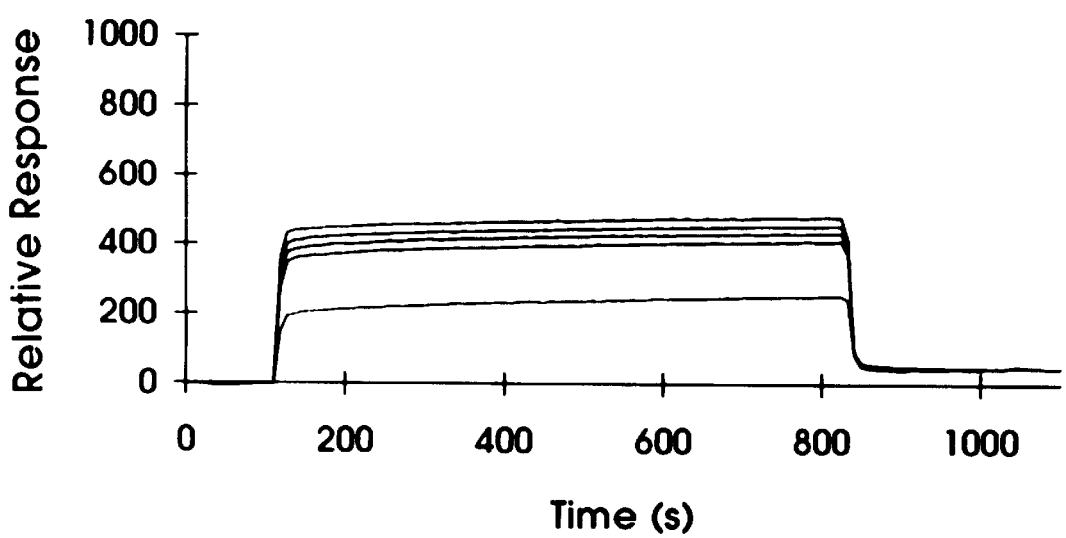
FIG. 5 is a sensorgram overlay plot of the non-binding control BSA.

The sensorgram overlay plots in FIGS. 2 to 5 show bovine fetuin binding in response units (R.U.) to immobilized TGF-β1 (FIG. 2); and to immobilized BMP-2 (FIG. 4). Each line from bottom to top represents increasing concentrations of injected analyte as detailed below. FIGS. 3 and 5 show the non-binding controls human transferrin passed over immobilized TGF-β1 and BSA passed over immobilized BMP-2, respectively. The large change in response at the beginning and end of injection is due to the change in refractive index caused by the protein in the injected buffer and does not indicate binding. Fetuin binding to TGF-β1 and BMP-2 is indicated by i) the increasing response with time during the injection, and ii) injection of increasing fetuin concentrations results in an incremental increase in response after the end of each injection. The fetuin—BMP-2 interaction shown in FIG. 4 does not come to equilibrium, whereas in FIG. 2 the lower affinity fetuin—TGF-β1 binding does come to equilibrium. Equilibrium is attained when the change in response with time is zero, as seen in panel (A) after approximately 200 seconds of fetuin binding to TGF-β1. Another control experiment showed that fetuin did not bind when a non-specific protein was immobilized (data not shown).

Analysis of the non-equilibrium binding data (See Example 5) revealed an association rate (k$_{ass}$) for fetuin—TGF-β1 binding of 670 M$^{-1}$s$^{-1}$ and a dissociation rate (k$_{diss}$) of 1.6×10$^{-3}$s$^{-1}$ (Table 1). Using the data in FIG. 2, Scatchard type analysis for steady-state fetuin—TGF-β1 binding produced a K$_D$ value of 4.6×10$^{-6}$M (data not shown), and the value 2.4×10$^{-6}$M was obtained from K$_D$=k$_{diss}$/k$_{ass}$. This measure of fetuin—TGF-β1 affinity is similar to the IC$_{50}$ for fetuin neutralization of TGF-β1 activity (FIG. 1), and is consistent with the view that fetuin neutralizes TGF-β1 activity by binding directly to the cytokine. Fetuin bound to the closely related cytokine TGF-β2, with similar affinity (Table 1).

Fetuin also bound to immobilized BMP-2 (FIG. 4), a TGF-β superfamily-member with 38% amino acid sequence identity to TGF-β1 (J. M. Wozney, V. Rosen, A. J. Celeste, L. M. Mitsock, M. J. Whitters, et al, Science 242, 1528 (1988) and V. Rosen, R. S. Thies, TIG 8, 97 (1992)). The affinity of fetuin binding to BMP-2 was approximately 100× greater ($K_D$=3.6×10$^{-8}$M) than fetuin binding to TGF-β1. Both interactions showed a similar on-rate ($k_{ass}$=1.7×10$^3$ M$^{-1}$s$^{-1}$) but fetuin—BMP-2 had a much slower off-rate ($k_{diss}$= 6.2×10$^{-5}$ s$^{-1}$) (Table 1), accounting for most of the difference in affinity. Fetuin also bound to immobilized BMP-4 and BMP-6 with characteristic affinities that differed largely due to changes in off-rates (Table 1). It is interesting to note that affinities for fetuin binding to the five cytokines showed a direct correlation with amino acid homology to BMP-2, the cytokine with the highest affinity for fetuin (Table 1).

Thyroglobulin was also tested for binding to the BMPs and TGFβ in the BIAcore assay described above. Surprisingly, thyroglobulin bound with higher affinity than fetuin to the cytokines, showing the strongest interaction with BMP-2 ($K_D$=3.1×10$^{-9}$M). Thyroglobulin bound to BMP-2>BMP-4>TGF-β1>TGF-β2, a rank order similar to that observed for fetuin binding to these cytokines (Example 5, Table 1). Thyroglobulin is found at low levels in serum, and at much higher concentrations in the follicles of the thyroid where it is a precursor to thyroxine. TGFβ has been shown to inhibit thyroglobulin biosynthesis and thyroid cell proliferation in vitro (Colletta et al. Cancer Res. 49, 3457, 1989). In this context, the results of the present studies suggest that thyroglobulin may bind to and antagonize this action of TGFβ in the thyroid.

Example 3

Figure 6:
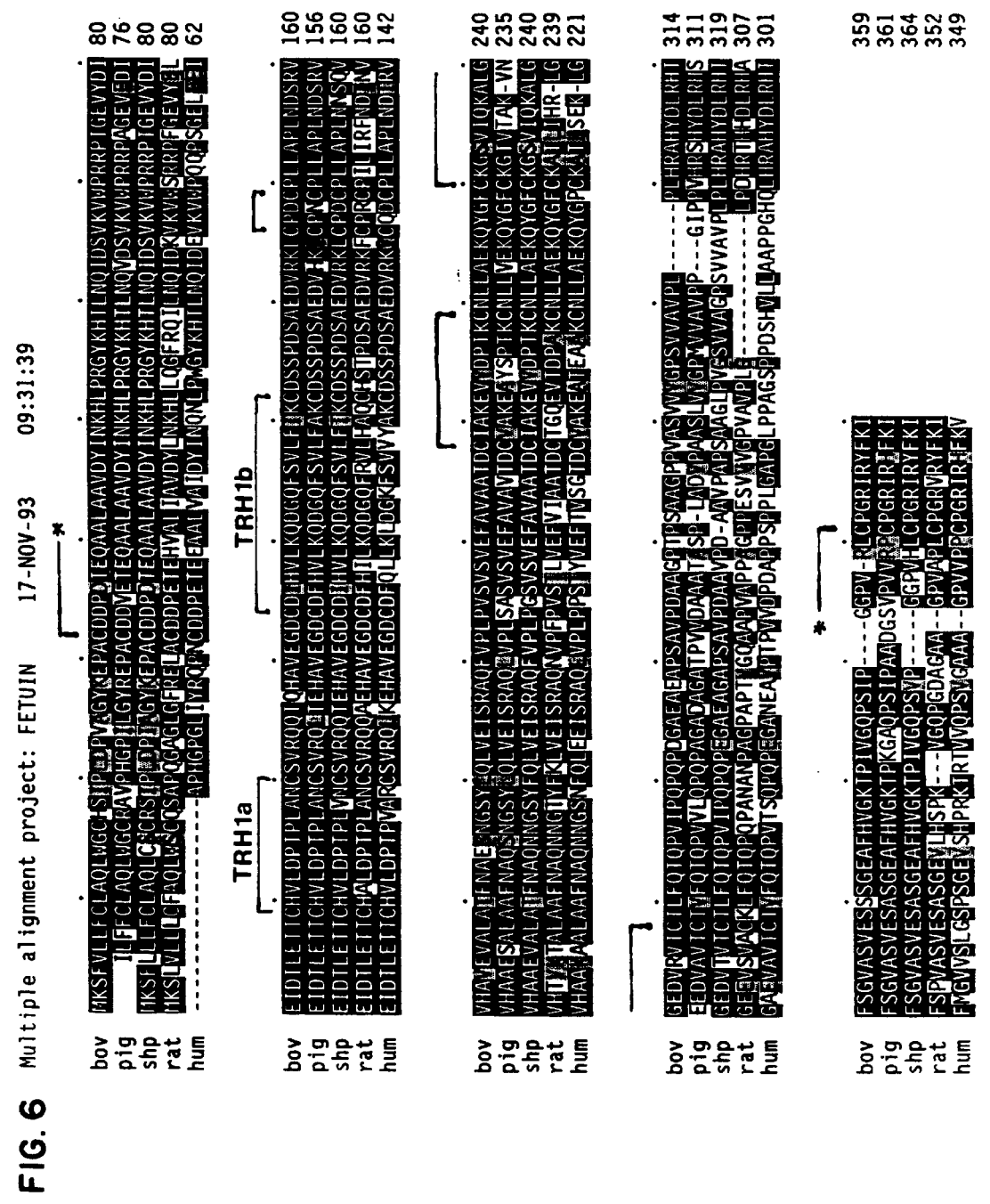
Figure 7:
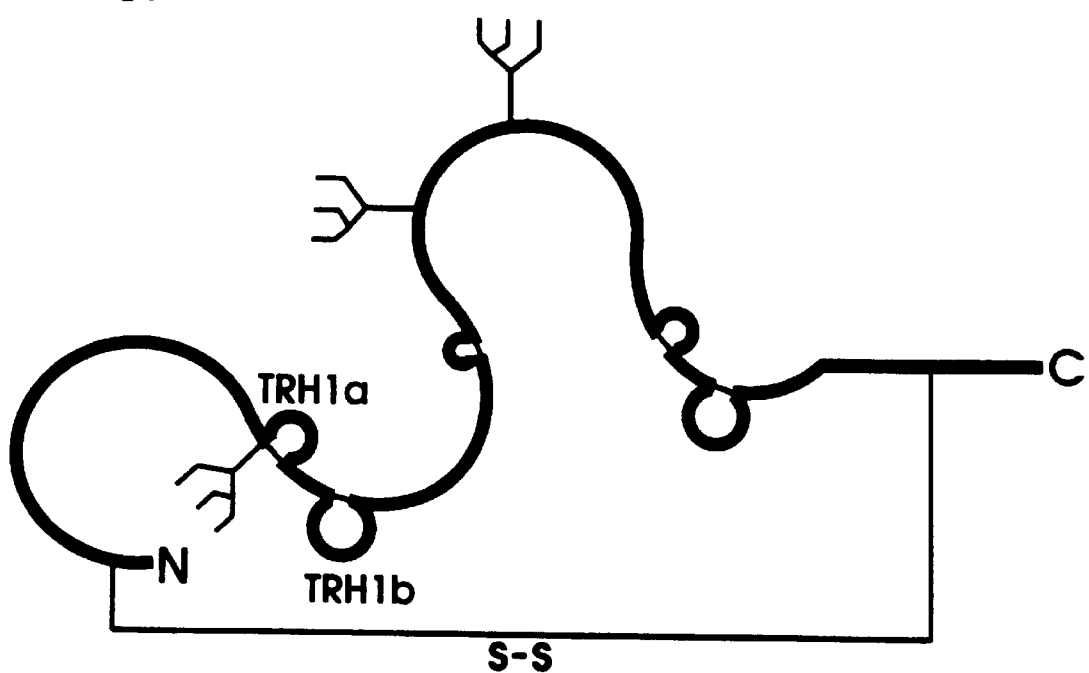
FIG. 7 is a schematic drawing of the disulfide loop structure of fetuin.

The amino acid sequences of fetuin and TGF-β receptor type I or type II were compared to identify a cytokine-binding domain. The fetuin and TβRII sequences were first aligned by positioning of the cysteine residues. The TGF-β type I (Tsk 7L) receptor shown in FIG. 8 is aligned with TβRII as in H. Y. Lin, X. -F. Wang, E. Ng-Eaton, R. A. Weinberg, H. F. Lodish, Cell 68, 775 (1992). The TGF-β type I (Tsk 7L) receptor shown in FIG. 8 is aligned with TβRII as in Ebner et al. Science 260, 1344–1348, 1993. Visual examination of the alignment revealed the 43 amino acid homology domain designated TGF-β Receptor II Homology 1 (TRH1) (FIG. 8). The intramolecular disulfide bonds of human fetuin have previously been determined (J. Kellermann, H. Haupt, E.-A. Auerswald, W. Müller-Esterl, J. Biol. Chem 264, 14121 (1989), and the TRH1 domain in fetuin contains two disulfide loops, designated a and b (FIGS. 7 and 8). The TRH1 domain and flanking sequences in fetuin are highly conserved across species (ie. human, bovine, sheep, rat, mouse), relative to the carboxy half of the molecule (See FIG. 6). Indeed, human fetuin (α2-HS glycoprotein) bound to BMP-2 with similar affinity as that of bovine fetuin (data not shown).

A search of the PIR protein sequence data base for other proteins containing the TRH1 domain was conducted using the GCG routine "findPatterns" and the following pattern: CX{8,14}(N,Q)X{12,16}CX{4,5}(K,R)X{2,6}(S,T)X{4,9}CX{0,2}DX{5,6}(D,E). The pattern was based on conserved amino acids between fetuin, TβRII, daf-1, and activin receptor type II. The search yielded 46 matches, most of which were extracellular domains of receptors or secreted glycoproteins and included, fetuins (n=5), kinnogens which are distant family members of the fetuins (J. Kellermann, H. Haupt, E. -A. Auerswald, W. Müller-Esterl, J. Biol. Chem 264, 14121 (1989)) (n=5), daf-1 (n=1), activin receptor type II (n=5), bovine thyroglobulin (L. Mercken, M.-J. Simons, S. Swillons, M. Massaer, G. Vassart, Nature 316, 647 (1985)) (n=1), EGF receptor (n=2), LDL receptor (n=1), IL-1 receptor (n=1) and drosophila crumbs (n=1). The number in brackets indicates the number of matches; for example fetuin from 5 species. Similarity in sequence between the TRH1b subdomains of TβRII, fetuin and thyroglobulin was striking, ranging from 63% to 71% (FIG. 8). Therefore, thyroglobulin was tested for binding to the BMPs and TGF-β in the BIAcore assay as described in Examples 1 and 2.

Example 4

The TGF-β and activin type I receptors lack the TRH1b sequence (FIG. 8), and do not bind ligand in the absence of type II receptors (R. Ebner, R.-H. Chen, L. Shum, S. Lawler, T. F. Zioncheck, et al, Science 260, 1344 (1993); L. Attisano, J. Carcamo, F. Ventura, F. M. S. Weis, J. Massague, et al, Cell 75, 671 (1993); P. Franzen, P. ten Dijke, H. Ichijo, H. Yamashita, P. Schulz, et al, Cell 75, 681 (1993), C. H. Bassing, J. M. Yingling, D. J. Howe, T. Wang, W. W. He, et al, Science 263, 87 (1994); and J. L. Wrana, L. Attisano, J. Carcamo, A. Zentella, J. Doody, et al, Cell 71, 1003 (1992)). This suggested that the TRH1b subdomain of type II receptors may be directly involved in cytokine binding. To examine this possibility, the 20 amino acid TRH1b peptides from both fetuin and TβRII were synthesized and a cyclized TRH1b peptide was prepared. The TRH1 peptides and cyclized peptide were tested for binding to TGF-β1 and BMP-2.

The cyclized TRH1b peptide was prepared by first reducing the peptide with DTT to remove dimers, trimers etc. and then bringing to a final concentration of 60 μM in 25 mM ammonium acetate (pH 8.5), After stirring in the dark for 30 min at 20° C. with 30 mM potassium ferricyanide, the peptide was mixed with AG3-X4A resin (BioRad) and filtered. Following lyopholization, the sample was desalted on a 50×2.5 cm column of Biogel P2 (BioRad) developed in water. Ion spray mass spectroscopy confirmed cyclization and did not detect the presence of multimers. Peptide, in 0.15M Tris pH 8.0, 0.15M NaCl, 2 mM EDTA, was reduced and alkylated by first boiling in 90 fold excess DTT for 10 min., followed by a 15 min incubation with 45 fold excess iodoacetamide (Pierce) in the dark with shaking. The sample was desalted on a P2 column. Ion spray mass spectroscopy confirmed reduction and alkylation of the peptide.

Figure 9:
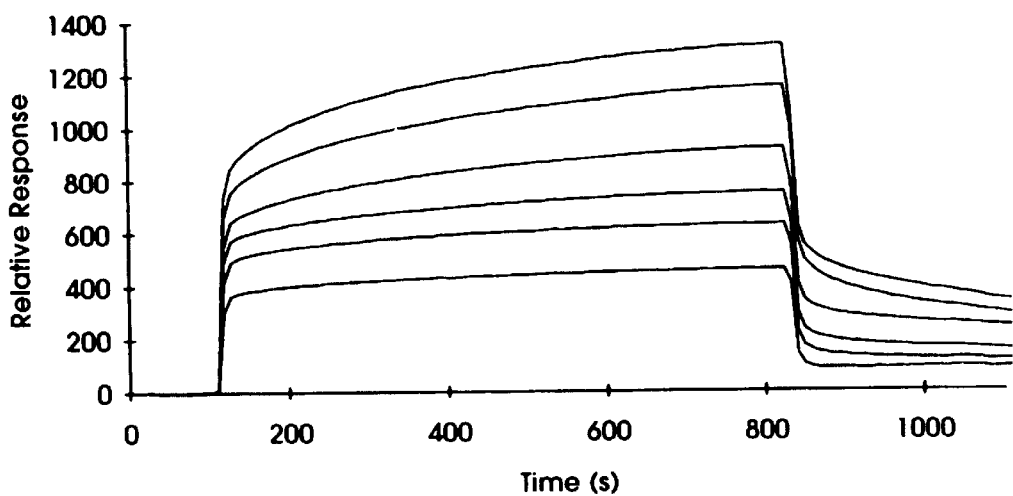
FIG. 9 is a sensorgram plot showing the binding of the disultide-looped TRH1b fetuin peptide to immobilized BMP-2.
Figure 10:
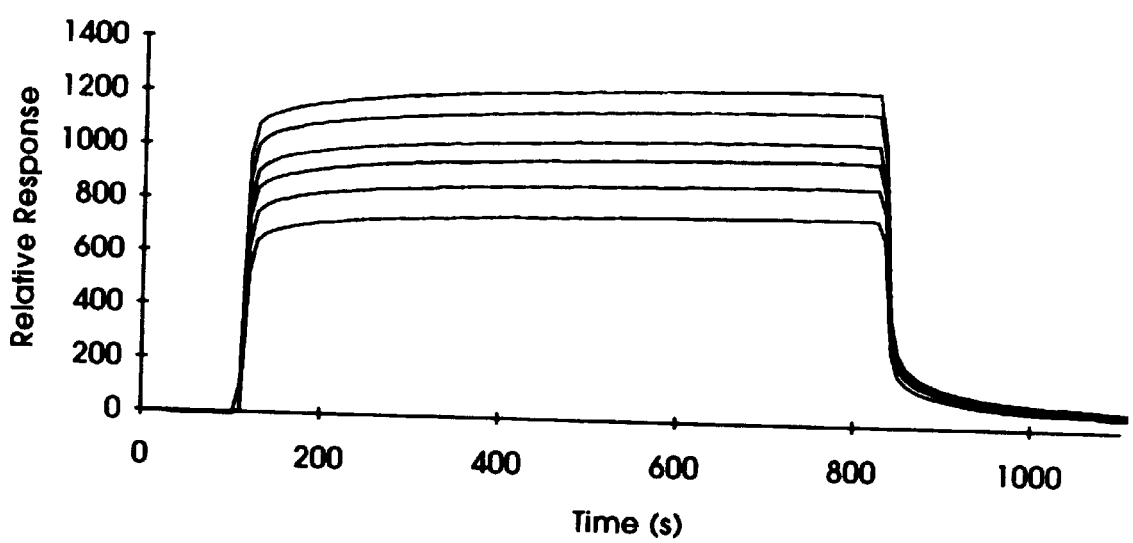
FIG. 10 is a sensorgram plot showing the lack of binding of reduced and alkylated TRH1b peptide.

FIG. 9 is a sensorgram overlay plot displaying binding of the disulfide-looped TRH1b fetuin peptide to immobilized BMP-2 (5300 R.U. immobilized) at 6 concentrations (87, 130, 174, 217, 283, and 348 μM). FIG. 10 is a sensorgram plot showing the lack of binding of reduced and alkylated THR1b peptide at the same concentrations. As the BIAcore signal measures mass, the lower molecular weight TRH1b peptide made it necessary to use near-saturating binding conditions to observe signal. Saturation was determined to be approximately 550 R.U. Competition of fetuin—BMP-2 binding by cyclized TRH1b peptide was observed, and to a much lesser extent, by the reduced and alkylated peptide (data not shown). Since TRH1b peptide is 1/20 the mass of fetuin, and therefore gives proportionately less signal per molecule bound, a reduction in response was observed when low concentrations of TRH1b were co-injected with fetuin, compared to fetuin alone. However, it was not possible to separate in a quantitative manner, the fetuin and THR1b peptide BIAcore signals observed with the non-equilibrium conditions experienced in these experiments.

The results demonstrate that the intramolecular disulfide-looped form of the fetuin TRH1b peptide bound directly to immobilized BMP-2 with a $K_D$=3.2×10$^6$M (FIG. 9, Table 1), and also competed for fetuin—BMP-2 binding in a dose dependent manner. However, no significant binding to BMP-2 was observed when this peptide was reduced and alkylated (FIG. 9). This is consistent with the observation that reduced and alkylated fetuin had diminished binding to BMP-2 and TGF-β1 compared to native fetuin (data not shown). The on-rate for disulfide-looped TRH1b peptide binding to BMP-2 is similar to that for intact fetuin, whereas the off-rate of TRH1b is 100 times faster (Table 1). This suggests that the TRH1b domain in fetuin is the major peptide motif involved in the initial recognition and binding to cytokine. Other portions of the fetuin protein may stabilize binding and/or the conformation of the TRH1b peptide loop, thereby slowing fetuin's off-rate when compared with the peptide.

If cytokine binding to TβRII is mediated by the TRH1b sequence, the known cytokine specificity of the receptors (J. L. Wrana, L. Attisano, J. Carcamo, A. Zentella, J. Doody, et al, Cell 71, 1003 (1992)) predicts that the peptide sequence from TβRII should bind to TGF-β1 with higher affinity then to BMP-2. BIAcore binding data confirmed this prediction (See Example 5 and Table 1). The cyclized TβRII peptide bound to TGF-β1 with higher affinity than to BMP-2 (ie. $K_D=5.2 \times 10^{-7}$M and $>10^{-5}$, respectively), a reversal of binding preference shown by the TRH1b peptide from fetuin (Table 1). This suggests that the TRH1b sequences can dictate ligand binding affinities and therefore ligand specificity.

Example 5

Binding constants for fetuin, thyroglobulin, and TRH! peptides with TGF-β1 and BMPs were determined. Data was analyzed using the BIA-evaluation software (Pharmacia Biosensor). The association rate constant, $k_{ass}$, was calculated by first plotting the change in response with time versus response (ie. dR/dT vs R). When the slope of the line from this graph is plotted versus analyte concentration (i.e d(dR/dT)/dR vs C), $k_{ass}$ is obtained from the slope of the line. The dissociation rate constant, $k_{diss}$, is obtained during the decrease in response with time after analyte injection is discontinued. Specifically, $k_{diss}$ was obtained from the slope of the line in a plot of $\ln(R_{t1}/R_{tn})$ vs time. The affinity constants were calculated from $K_D = k_{diss}/k_{ass}$. Variance for $k_{ass}$ is standard error of the linear regression plot, and for $k_{diss}$ values are the mean±range of 3 or more independent injections. Bracketed numbers in Table 1 are percent homology of the cytokines relative to BMP-2.

The experiments described in the Examples define a disulfide-looped motif common to TβRII, fetuin and thyroglobulin which mediates binding to two divergent members of the TGF-β superfamily. The TRH1 motif is conserved in the ligand-binding TβRII family members including activin type II[18] and daf-1 receptors, but is absent in the TGF-β/activin type I receptors; the latter are unable to bind cytokine in the absence of type II receptors. Fetuin and thyroglobulin have significantly higher affinities for BMP-2 than for TGF-β1, suggesting that variations in both TGF-βs and TRH1 sequences may dictate ligand-receptor/antagonist specificity through changes in binding-affinity. The results also suggest a hitherto unknown function for fetuin and thyroglobulin as antagonists of TGF-β superfamily members in vivo and may explain the mechanism for the broad biological activities ascribed to fetuin.

The present invention has been described in detail and with particular reference to the preferred embodiments; however, it will be understood by one having ordinary skill in the art that changes can be made thereto without departing from the spirit and scope thereof.

All publications, patents and patent applications are herein incorporated by reference in their entirety to the same extent as if each individual publication, patent or patent application was specifically and individually indicated to be incorporated by reference in its entirety.

Forming part of the present disclosure are the appended sequence listings.

TABLE 1

Binding constants for fetuin, thyroglobulin and TRH1b interactions with cytokines

| Analyte | Ligand | $k_{ass}$ (M$^{-1}$s$^{-1}$) | $k_{diss}$ (s$^{-1}$) | $K_D$ (M) |
|---|---|---|---|---|
| Fetuin | TGF-β1 (38%) | $6.7 \times 10^2 \pm 4.0 \times 10^2$ | $1.6 \times 10^{-3} \pm 0.4 \times 10^{-3}$ | $2.4 \times 10^{-6}$ |
| | TGF-β2 (36%) | $5.5 \times 10^2 \pm 1.2 \times 10^2$ | $3.2 \times 10^{-3} \pm 0.5 \times 10^{-3}$ | $5.8 \times 10^{-6}$ |
| | BMP-2 (100%) | $1.7 \times 10^3 \pm 0.3 \times 10^3$ | $6.2 \times 10^{-5} \pm 3.6 \times 10^{-5}$ | $3.6 \times 10^{-8}$ |
| | BMP-4 (86%) | $4.2 \times 10^3 \pm 0.2 \times 10^3$ | $5.8 \times 10^{-4} \pm 0.1 \times 10^{-4}$ | $1.4 \times 10^{-7}$ |
| | BMP-6 (57%) | $2.9 \times 10^3 \pm 0.5 \times 10^3$ | $2.5 \times 10^{-3} \pm 0.5 \times 10^{-3}$ | $8.6 \times 10^{-7}$ |
| Thyroglobulin | TGF-β1 | $2.8 \times 10^3 \pm 1.0 \times 10^3$ | $1.9 \times 10^{-3} \pm 0.8 \times 10^{-3}$ | $6.8 \times 10^{-7}$ |
| | TGF-β2 | $1.3 \times 10^3 \pm 0.6 \times 10^3$ | $5.0 \times 10^{-3} \pm 0.5 \times 10^{-3}$ | $3.8 \times 10^{-6}$ |
| | BMP-2 | $3.2 \times 10^4 \pm 0.2 \times 10^4$ | $1.0 \times 10^{-4} \pm 0.1 \times 10^{-4}$ | $3.1 \times 10^{-9}$ |
| | BMP-4 | $5.4 \times 10^4 \pm 0.7 \times 10^4$ | $1.1 \times 10^{-3} \pm 0.4 \times 10^{-3}$ | $2.0 \times 10^{-8}$ |
| TRH1b (fetuin) | BMP-2 | $1.6 \times 10^3 \pm 0.5 \times 10^3$ | $5.1 \times 10^{-3} \pm 1.1 \times 10^{-3}$ | $3.2 \times 10^{-6}$ |
| | TGF-β1 | — | — | $>10^{-5}$ |
| (reduced & alkylated) | BMP-2 | — | — | $>10^{-5}$ |
| TRH1b (TβRII) | BMP-2 | — | — | $>10^{-5}$ |
| | TGF-β1 | $3.7 \times 10^3 \pm 2.9 \times 10^3$ | $1.9 \times 10^{-3} \pm 0.5 \times 10^{-3}$ | $5.2 \times 10^{-7}$ |
| (reduced & alkylated) | TGFβ1 | — | — | $>10^{-5}$ |

Binding constants for fetuin, thyroglobulin and TRH1b peptides with TGF-β and BMPs. Data was analyzed using the BIA-evaluation software (Pharmacia Biosensor). The association rate constant, $k_{ass}$, was calculated by first plotting the change in response with time versus response (ie. dR/dT vs R). When the slope of the line from this graph is plotted versus analyte concentration (i.e d(dR/dT)/dR vs C), $k_{ass}$ is obtained from the slope of the line. The dissociation rate constant, $k_{diss}$, is obtained during the decrease in response with time after analyte injection is discontinued. Specifically, $k_{diss}$ was obtained from the slope of the line in a plot of $\ln(R_{t1}/R_x)$ vs time. The affinty constants were calculated from $K_D = k_{diss}/k_{ass}$. Variance for $k_{ass}$ is standard error of the linear regression plot, and for $k_{diss}$ values are the mean ± range of 3 or more independent injections. Bracketed numbers are percent homology of the cytokines relative to BMP-2.

We claim:

1. A composition comprising a TGFβ binding compound consisting essentially of a TGFβ receptor II homology 1 (TRH1) domain of fetuin as shown in SEQ. ID. NO. 2, the TRH1 domain from the TGFβ type II receptor as shown in SEQ. ID. NO. 3, or the TRH1 domain from thyroglobulin as shown in SEQ. ID. NO. 4.

2. A composition comprising a TGFβ binding compound consisting essentially of a TGFβ receptor II homology 1b (TRH1b) subdomain from fetuin, the TGFβ type II receptor, or thyroglobulin as shown in SEQ. ID. NOS. 5, 6, or 7, respectively.

3. A composition comprising a TGFβ binding compound consisting essentially of two or more of a TGFβ receptor II homology 1 (TRH1) domain of fetuin as shown in SEQ. ID. NO. 2, the TRH1 domain from the TGFβ type II receptor as shown in SEQ. ID. NO. 3, or the TRH1 domain from thyroglobulin as shown in SEQ. ID. NO. 4.

4. A composition comprising a TGFβ binding compound consisting essentially of two or more of a TGFβ receptor II homology 1b (TRH1b) subdomain from fetuin, the TGFβ type II receptor, or thyroglobulin as shown in SEQ. ID. NOS. 5, 6, and 7, respectively.

5. A composition comprising at least one TGFβ receptor II homology 1b (TRH1b) subdomain and a carrier, auxiliary or excipient, wherein the TRH1 subdomain mediates the binding of a TGF-β binding compound to a cytokine which is a member of a family selected from the group consisting of the TGFβ family, the inhibin family, the DPP/VG1 family, and the Mullerian Inhibiting Substance Family, and wherein the TRH1b subdomain has a sequence with the following amino acid patter: Cys-$X_j$-Lys/Arg-$X_k$-Ser/Thr-$X_l$-Cys-$X_m$-Asp-$X_n$-Asp/Glu, wherein $X_j$, $X_k$, $X_l$, $X_m$ and $X_n$ represent any amino acid and j is 4 to 5, k is 2 to 6, l is 4 to 9, m is 0 to 2, and n is 5 to 6.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
( A ) LENGTH: 567 amino acids
( B ) TYPE: amino acid
( C ) STRANDEDNESS:
( D ) TOPOLOGY: unknown ( i i ) MOLECULE TYPE: peptide ( v i ) ORIGINAL SOURCE:
( A ) ORGANISM: Homo sapiens ( v i i ) IMMEDIATE SOURCE:
( A ) LIBRARY: Lambda zapII ( x i ) SEQUENCE DESCRIPTION: SEQ ID NO:1:

```
Met Gly Arg Gly Leu Leu Arg Gly Leu Trp Pro Leu His Ile Val Leu
 1               5                  10                  15

Trp Thr Arg Ile Ala Ser Thr Ile Pro Pro His Val Gln Lys Ser Val
                20                  25                  30

Asn Asn Asp Met Ile Val Thr Asp Asn Asn Gly Ala Val Lys Phe Pro
             35                  40                  45

Gln Leu Cys Lys Phe Cys Asp Val Arg Phe Ser Thr Cys Asp Asn Gln
         50                  55                  60

Lys Ser Cys Met Ser Asn Cys Ser Ile Thr Ser Ile Cys Glu Lys Pro
 65                  70                  75                  80

Gln Glu Val Cys Val Ala Val Trp Arg Lys Asn Asp Glu Asn Ile Thr
                 85                  90                  95

Leu Glu Thr Val Cys His Asp Pro Lys Leu Pro Tyr His Asp Phe Ile
                100                 105                 110

Leu Glu Asp Ala Ala Ser Pro Lys Cys Ile Met Lys Glu Lys Lys Lys
             115                 120                 125

Pro Gly Glu Thr Phe Phe Met Cys Ser Cys Ser Ser Asp Glu Cys Asn
    130                 135                 140

Asp Asn Ile Ile Phe Ser Glu Glu Tyr Asn Thr Ser Asn Pro Asp Leu
145                 150                 155                 160

Leu Leu Val Ile Phe Gln Val Thr Gly Ile Ser Leu Leu Pro Pro Leu
                165                 170                 175

Gly Val Ala Ile Ser Val Ile Ile Ile Phe Tyr Cys Tyr Arg Val Asn
             180                 185                 190

Arg Gln Gln Lys Leu Ser Ser Thr Trp Glu Thr Gly Lys Thr Arg Lys
         195                 200                 205

Leu Met Glu Phe Ser Glu His Cys Ala Ile Ile Leu Glu Asp Asp Arg
    210                 215                 220

Ser Asp Ile Ser Ser Thr Cys Ala Asn Asn Ile Asn His Asn Thr Glu
225                 230                 235                 240

Leu Leu Pro Ile Glu Leu Asp Thr Leu Val Gly Lys Gly Arg Phe Ala
                245                 250                 255

Glu Val Tyr Lys Ala Lys Leu Lys Gln Asn Thr Ser Glu Gln Phe Glu
             260                 265                 270

Thr Val Ala Val Lys Ile Phe Pro Tyr Glu Glu Tyr Ala Ser Trp Lys
         275                 280                 285
```

```
Thr  Glu  Lys  Asp  Ile  Phe  Ser  Asp  Ile  Asn  Leu  Lys  His  Glu  Asn  Ile
     290                 295                      300

Leu  Gln  Phe  Leu  Thr  Ala  Glu  Glu  Arg  Lys  Thr  Glu  Leu  Gly  Lys  Gln
305                      310                 315                           320

Tyr  Trp  Leu  Ile  Thr  Ala  Phe  His  Ala  Lys  Gly  Asn  Leu  Gln  Glu  Tyr
                    325                      330                           335

Leu  Thr  Arg  His  Val  Ile  Ser  Trp  Glu  Asp  Leu  Arg  Lys  Leu  Gly  Ser
               340                      345                      350

Ser  Leu  Ala  Arg  Gly  Ile  Ala  His  Leu  His  Ser  Asp  His  Thr  Pro  Cys
          355                      360                      365

Gly  Arg  Pro  Lys  Met  Pro  Ile  Val  His  Arg  Asp  Leu  Lys  Ser  Ser  Asn
     370                      375                      380

Ile  Leu  Val  Lys  Asn  Asp  Leu  Thr  Cys  Cys  Leu  Cys  Asp  Phe  Gly  Leu
385                      390                      395                      400

Ser  Leu  Arg  Leu  Asp  Pro  Thr  Leu  Ser  Val  Asp  Asp  Leu  Ala  Asn  Ser
                    405                      410                      415

Gly  Gln  Val  Gly  Thr  Ala  Arg  Tyr  Met  Ala  Pro  Glu  Val  Leu  Glu  Ser
               420                      425                      430

Arg  Met  Asn  Leu  Glu  Asn  Ala  Glu  Ser  Phe  Lys  Gln  Thr  Asp  Val  Tyr
          435                      440                      445

Ser  Met  Ala  Leu  Val  Leu  Trp  Glu  Met  Thr  Ser  Arg  Cys  Asn  Ala  Val
     450                      455                      460

Gly  Glu  Val  Lys  Asp  Tyr  Glu  Pro  Pro  Phe  Gly  Ser  Lys  Val  Arg  Glu
465                      470                      475                      480

His  Pro  Cys  Val  Glu  Ser  Met  Lys  Asp  Asn  Val  Leu  Arg  Asp  Arg  Gly
                    485                      490                      495

Arg  Pro  Glu  Ile  Pro  Ser  Phe  Trp  Leu  Asn  His  Gln  Gly  Ile  Gln  Met
               500                      505                      510

Val  Cys  Glu  Thr  Leu  Thr  Glu  Cys  Trp  Asp  His  Asp  Pro  Glu  Ala  Arg
          515                      520                      525

Leu  Thr  Ala  Gln  Cys  Val  Ala  Glu  Arg  Phe  Ser  Glu  Leu  Glu  His  Leu
     530                      535                      540

Asp  Arg  Leu  Ser  Gly  Arg  Ser  Cys  Ser  Glu  Glu  Lys  Ile  Pro  Glu  Asp
545                      550                      555                      560

Gly  Ser  Leu  Asn  Thr  Thr  Lys
                    565
```

( 2 ) INFORMATION FOR SEQ ID NO:2:

( i ) SEQUENCE CHARACTERISTICS:
        ( A ) LENGTH: 45 amino acids
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM: Homo sapiens ( v i i ) IMMEDIATE SOURCE:
        ( A ) LIBRARY: lambda zapII ( x i ) SEQUENCE DESCRIPTION: SEQ ID NO:2:

```
Cys  His  Val  Leu  Asp  Pro  Thr  Pro  Leu  Ala  Asn  Cys  Ser  Val  Arg  Gln
1                   5                        10                      15

Gln  Thr  Gln  His  Ala  Val  Glu  Gly  Asp  Cys  Asp  Ile  His  Val  Leu  Lys
               20                       25                       30
```

Gln Asp Gly Gln Phe Ser Val Leu Phe Thr Lys Cys Asp
         35                      40                      45

( 2 ) INFORMATION FOR SEQ ID NO:3:

( i ) SEQUENCE CHARACTERISTICS:
        ( A ) LENGTH: 43 amino acids
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM: Homo sapiens ( v i i ) IMMEDIATE SOURCE:
        ( A ) LIBRARY: lambda zapII ( x i ) SEQUENCE DESCRIPTION: SEQ ID NO:3:

Cys Asp Asn Gln Lys Ser Cys Met Ser Asn Cys Ser Ile Thr Ser Ile
1                5                       10                      15

Cys Glu Lys Pro Gln Glu Val Cys Val Ala Val Trp Arg Lys Asn Asp
            20                      25                      30

Glu Asn Ile Thr Leu Glu Thr Val Cys His Asp
         35                      40

( 2 ) INFORMATION FOR SEQ ID NO:4:

( i ) SEQUENCE CHARACTERISTICS:
        ( A ) LENGTH: 44 amino acids
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM: Homo sapiens ( v i i ) IMMEDIATE SOURCE:
        ( A ) LIBRARY: lambda zapII ( x i ) SEQUENCE DESCRIPTION: SEQ ID NO:4:

Cys Ser Ala Asp Tyr Ser Gly Leu Leu Leu Ala Phe Gln Val Phe Leu
1                5                       10                      15

Leu Asp Glu Leu Thr Ala Arg Gly Phe Cys Gln Ile Gln Val Lys Thr
            20                      25                      30

Ala Gly Thr Pro Val Ser Ile Pro Val Cys Asp Asp
         35                      40

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS:
        ( D ) TOPOLOGY: unknown ( i i ) MOLECULE TYPE: peptide ( v i ) ORIGINAL SOURCE:
        ( A ) ORGANISM: Homo sapiens ( v i i ) IMMEDIATE SOURCE:
        ( A ) LIBRARY: Lambda zapII ( x i ) SEQUENCE DESCRIPTION: SEQ ID NO:5:

Cys Asp Ile His Val Leu Lys Gln Asp Gly Gln Phe Ser Val Leu Phe
1                5                       10                      15

```
            Thr  Lys  Cys  Asp
                        20
```

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS:
        (D) TOPOLOGY: unknown (ii) MOLECULE TYPE: peptide (vi) ORIGINAL SOURCE:
        (A) ORGANISM: Homo sapiens (vii) IMMEDIATE SOURCE:
        (A) LIBRARY: Lambda zapII (xi) SEQUENCE DESCRIPTION: SEQ ID NO:6:

```
Cys  Val  Ala  Val  Trp  Arg  Lys  Asn  Asp  Glu  Asn  Ile  Thr  Leu  Glu  Thr
 1                    5                        10                       15
Val  Cys  His  Asp
                20
```

(2) INFORMATION FOR SEQ ID NO:7:

(i) SEQUENCE CHARACTERISTICS:
        (A) LENGTH: 19 amino acids
        (B) TYPE: amino acid
        (C) STRANDEDNESS:
        (D) TOPOLOGY: unknown (ii) MOLECULE TYPE: peptide (vi) ORIGINAL SOURCE:
        (A) ORGANISM: Homo sapiens (vii) IMMEDIATE SOURCE:
        (A) LIBRARY: Lambda zapII (xi) SEQUENCE DESCRIPTION: SEQ ID NO:7:

```
Cys  Gln  Ile  Gln  Val  Lys  Thr  Ala  Gly  Thr  Pro  Val  Ser  Ile  Pro  Val
 1                    5                        10                       15
Cys  Asp  Asp
```

(2) INFORMATION FOR SEQ ID NO:8:

(i) SEQUENCE CHARACTERISTICS:
        (A) LENGTH: 359 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Bovine (xi) SEQUENCE DESCRIPTION: SEQ ID NO:8:

```
Met  Lys  Ser  Phe  Val  Leu  Leu  Phe  Cys  Leu  Ala  Gln  Leu  Trp  Gly  Cys
 1                    5                        10                       15
His  Ser  Ile  Pro  Leu  Asp  Pro  Val  Ala  Gly  Tyr  Lys  Glu  Pro  Ala  Cys
                20                       25                       30
Asp  Asp  Pro  Asp  Thr  Glu  Gln  Ala  Ala  Leu  Ala  Ala  Val  Asp  Tyr  Ile
                35                       40                       45
Asn  Lys  His  Leu  Pro  Arg  Gly  Tyr  Lys  His  Thr  Leu  Asn  Gln  Ile  Asp
                50                       55                       60
```

|   |   |   |   |   |   |   |   |   |   |   |   |   |   |   |   |
|---|---|---|---|---|---|---|---|---|---|---|---|---|---|---|---|
| Ser 65 | Val | Lys | Val | Trp | Pro 70 | Arg | Arg | Pro | Thr | Glu 75 | Val | Tyr | Asp | Ile 80 |
| Glu | Ile | Asp | Thr | Leu 85 | Glu | Thr | Thr | Cys | His 90 | Val | Leu | Asp | Pro | Thr 95 | Pro |
| Leu | Ala | Asn | Cys 100 | Ser | Val | Arg | Gln | Gln 105 | Thr | Gln | His | Ala | Val 110 | Glu | Gly |
| Asp | Cys | Asp 115 | Ile | His | Val | Leu | Lys 120 | Gln | Asp | Gly | Gln | Phe 125 | Ser | Val | Leu |
| Phe | Ile 130 | Lys | Cys | Asp | Ser | Ser 135 | Pro | Asp | Ser | Ala | Glu 140 | Asp | Val | Arg | Lys |
| Leu 145 | Cys | Pro | Asp | Cys | Pro 150 | Leu | Leu | Ala | Pro | Leu 155 | Asn | Asp | Ser | Arg | Val 160 |
| Val | His | Ala | Val | Glu 165 | Val | Ala | Leu | Ala | Thr 170 | Phe | Asn | Ala | Glu | Ser 175 | Asn |
| Gly | Ser | Tyr | Leu 180 | Gln | Leu | Val | Glu | Ile 185 | Ser | Arg | Ala | Gln | Phe 190 | Val | Pro |
| Leu | Pro | Val 195 | Ser | Val | Ser | Val | Glu 200 | Phe | Ala | Val | Ala | Ala 205 | Thr | Asp | Cys |
| Ile | Ala | Lys 210 | Glu | Val | Val | Asp | Pro 215 | Thr | Lys | Cys | Asn | Leu 220 | Leu | Ala | Glu |
| Lys 225 | Gln | Tyr | Gly | Phe | Cys 230 | Lys | Gly | Ser | Val | Ile 235 | Gln | Lys | Ala | Leu | Gly 240 |
| Gly | Glu | Asp | Val | Arg 245 | Val | Thr | Cys | Thr | Leu 250 | Phe | Gln | Thr | Gln | Pro 255 | Val |
| Ile | Pro | Gln | Pro 260 | Gln | Pro | Asp | Gly | Ala 265 | Glu | Ala | Glu | Ala | Pro 270 | Ser | Ala |
| Val | Pro | Asp 275 | Ala | Ala | Gly | Pro | Thr 280 | Pro | Ser | Ala | Ala | Gly 285 | Pro | Pro | Val |
| Ala | Ser | Val 290 | Val | Val | Gly | Pro 295 | Ser | Val | Val | Ala | Val 300 | Pro | Leu | Pro | Leu |
| His 305 | Arg | Ala | His | Tyr | Asp 310 | Leu | Arg | His | Thr | Phe 315 | Ser | Gly | Val | Ala | Ser 320 |
| Val | Glu | Ser | Ser | Ser 325 | Gly | Glu | Ala | Phe | His 330 | Val | Gly | Lys | Thr | Pro 335 | Ile |
| Val | Gly | Gln | Pro 340 | Ser | Ile | Pro | Gly | Gly 345 | Pro | Val | Arg | Leu | Cys 350 | Pro | Gly |
| Arg 355 | Ile | Arg | Tyr | Phe | Lys | Ile |   |   |   |   |   |   |   |   |   |

( 2 ) INFORMATION FOR SEQ ID NO:9:

( i ) SEQUENCE CHARACTERISTICS:
        ( A ) LENGTH: 361 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Pig ( x i ) SEQUENCE DESCRIPTION: SEQ ID NO:9:

|   |   |   |   |   |   |   |   |   |   |   |   |   |   |   |   |
|---|---|---|---|---|---|---|---|---|---|---|---|---|---|---|---|
| Ile 1 | Leu | Phe | Phe | Cys 5 | Leu | Ala | Gln | Leu | Trp 10 | Gly | Cys | Arg | Ala | Val 15 | Pro |
| His | Gly | Pro | Ile 20 | Leu | Gly | Tyr | Arg | Glu 25 | Pro | Ala | Cys | Asp | Asp 30 | Val | Glu |

```
Thr  Glu  Gln  Ala  Ala  Leu  Ala  Ala  Val  Asp  Tyr  Ile  Asn  Lys  His  Leu
          35                       40                  45

Pro  Arg  Gly  Tyr  Lys  His  Thr  Leu  Asn  Gln  Ile  Asp  Ser  Val  Lys  Val
     50                       55                  60

Trp  Pro  Arg  Arg  Pro  Ala  Gly  Glu  Val  Phe  Asp  Ile  Glu  Ile  Asp  Thr
65                       70                  75                            80

Leu  Glu  Thr  Thr  Cys  His  Val  Leu  Asp  Pro  Thr  Pro  Leu  Ala  Asn  Cys
               85                       90                            95

Ser  Val  Arg  Gln  Leu  Thr  Glu  His  Ala  Val  Glu  Gly  Asp  Cys  Asp  Phe
               100                      105                      110

His  Val  Leu  Lys  Gln  Asp  Gly  Gln  Phe  Ser  Val  Leu  Phe  Ala  Lys  Cys
          115                      120                 125

Asp  Ser  Ser  Pro  Asp  Ser  Ala  Glu  Asp  Val  His  Lys  Tyr  Cys  Pro  Asn
     130                      135                      140

Cys  Pro  Leu  Leu  Ala  Pro  Leu  Asn  Asp  Ser  Arg  Val  Val  His  Ala  Ala
145                      150                      155                      160

Glu  Ser  Ala  Leu  Ala  Ala  Phe  Asn  Ala  Gln  Ser  Asn  Gly  Ser  Tyr  Leu
               165                      170                      175

Gln  Leu  Val  Glu  Ile  Ser  Arg  Ala  Gln  Leu  Val  Pro  Leu  Ser  Ala  Ser
               180                      185                      190

Val  Ser  Val  Glu  Phe  Ala  Val  Ala  Val  Thr  Asp  Cys  Val  Ala  Lys  Glu
          195                      200                      205

Ala  Tyr  Ser  Pro  Thr  Lys  Cys  Asn  Leu  Leu  Val  Glu  Lys  Gln  Tyr  Gly
     210                      215                      220

Phe  Cys  Lys  Gly  Thr  Val  Thr  Ala  Lys  Val  Asn  Glu  Glu  Asp  Val  Ala
225                      230                      235                      240

Val  Thr  Cys  Thr  Val  Phe  Gln  Thr  Gln  Pro  Val  Val  Leu  Gln  Pro  Gln
                    245                      250                      255

Pro  Ala  Gly  Ala  Asp  Ala  Gly  Ala  Thr  Pro  Val  Val  Asp  Ala  Ala  Ala
               260                      265                      270

Thr  Ala  Ser  Pro  Leu  Ala  Asp  Val  Pro  Ala  Ala  Ser  Leu  Val  Val  Gly
          275                      280                      285

Pro  Met  Val  Val  Ala  Val  Pro  Pro  Gly  Ile  Pro  Pro  Val  His  Arg  Ser
     290                      295                      300

His  Tyr  Asp  Leu  Arg  His  Ser  Phe  Ser  Gly  Val  Ala  Ser  Val  Glu  Ser
305                      310                      315                      320

Ala  Ser  Gly  Glu  Ala  Phe  His  Val  Gly  Lys  Thr  Pro  Lys  Gly  Ala  Gln
                    325                      330                      335

Pro  Ser  Ile  Pro  Ala  Ala  Asp  Gly  Ser  Val  Pro  Val  Val  Arg  Pro  Cys
               340                      345                      350

Pro  Gly  Arg  Ile  Arg  His  Phe  Lys  Ile
          355                      360
```

( 2 ) INFORMATION FOR SEQ ID NO:10:

( i ) SEQUENCE CHARACTERISTICS:
        ( A ) LENGTH: 364 amino acids
        ( B ) TYPE: amino acid
        ( C ) STRANDEDNESS: single
        ( D ) TOPOLOGY: linear ( i i ) MOLECULE TYPE: peptide ( v i ) ORIGINAL SOURCE:
        ( A ) ORGANISM: Sheep ( x i ) SEQUENCE DESCRIPTION: SEQ ID NO:10:

| | | | | | | | | | | | | | | | |
|---|---|---|---|---|---|---|---|---|---|---|---|---|---|---|---|
| Met<br>1 | Lys | Ser | Phe | Leu<br>5 | Leu | Leu | Phe | Cys | Leu<br>10 | Ala | Gln | Leu | Cys | Ser<br>15 | Cys |
| Arg | Ser | Ile | Pro<br>20 | Leu | Asp | Pro | Ile | Ala<br>25 | Gly | Tyr | Lys | Glu | Pro<br>30 | Ala | Cys |
| Asp | Asp | Pro<br>35 | Asp | Thr | Glu | Gln | Ala<br>40 | Ala | Leu | Ala | Ala | Val<br>45 | Asp | Tyr | Ile |
| Asn | Lys<br>50 | His | Leu | Pro | Arg | Gly<br>55 | Tyr | Lys | His | Thr | Leu<br>60 | Asn | Gln | Ile | Asp |
| Ser<br>65 | Val | Lys | Val | Trp | Pro<br>70 | Arg | Arg | Pro | Thr | Gly<br>75 | Glu | Val | Tyr | Asp | Ile<br>80 |
| Glu | Ile | Asp | Thr | Leu<br>85 | Glu | Thr | Thr | Cys | His<br>90 | Val | Leu | Asp | Pro | Thr<br>95 | Pro |
| Leu | Val | Asn | Cys<br>100 | Ser | Val | Arg | Gln | Gln<br>105 | Thr | Glu | His | Ala | Val<br>110 | Glu | Gly |
| Asp | Cys | Asp<br>115 | Ile | His | Val | Leu | Lys<br>120 | Gln | Asp | Gly | Gln | Phe<br>125 | Ser | Val | Leu |
| Phe | Thr<br>130 | Lys | Cys | Asp | Ser | Ser<br>135 | Pro | Asp | Ser | Ala | Glu<br>140 | Asp | Val | Arg | Lys |
| Leu<br>145 | Cys | Pro | Asp | Cys | Pro<br>150 | Leu | Leu | Ala | Pro | Leu<br>155 | Asn | Asn | Ser | Gln | Val<br>160 |
| Val | His | Ala | Ala | Glu<br>165 | Val | Ala | Leu | Ala | Thr<br>170 | Phe | Asn | Ala | Gln | Asn<br>175 | Asn |
| Gly | Ser | Tyr | Phe<br>180 | Gln | Leu | Val | Glu | Ile<br>185 | Ser | Arg | Ala | Gln | Phe<br>190 | Val | Pro |
| Leu | Pro | Gly<br>195 | Ser | Val | Ser | Val | Glu<br>200 | Phe | Ala | Val | Ala | Ala<br>205 | Thr | Asp | Cys |
| Ile | Ala<br>210 | Lys | Glu | Val | Val | Asp<br>215 | Pro | Thr | Lys | Cys | Asn<br>220 | Leu | Leu | Ala | Glu |
| Lys<br>225 | Gln | Tyr | Gly | Phe | Cys<br>230 | Lys | Gly | Ser | Val | Ile<br>235 | Gln | Lys | Ala | Leu | Gly<br>240 |
| Gly | Glu | Asp | Val | Thr<br>245 | Val | Thr | Cys | Thr | Leu<br>250 | Phe | Gln | Thr | Gln<br>255 | Pro | Val |
| Ile | Pro | Gln | Pro<br>260 | Gln | Pro | Glu | Gly | Ala<br>265 | Glu | Ala | Gly | Ala | Pro<br>270 | Ser | Ala |
| Val | Pro | Asp<br>275 | Ala | Ala | Val | Pro | Asp<br>280 | Ala | Ala | Val | Pro | Ala<br>285 | Pro | Ser | Ala |
| Ala | Gly<br>290 | Leu | Pro | Val | Gly | Ser<br>295 | Val | Val | Ala | Gly | Pro<br>300 | Ser | Val | Val | Ala |
| Val | Pro<br>305 | Leu | Pro | Leu | His | Arg<br>310 | Ala | His | Tyr | Asp | Leu<br>315 | Arg | His | Thr | Phe<br>320 |
| Ser | Gly | Val | Ala | Ser<br>325 | Val | Glu | Ser | Ala | Ser<br>330 | Gly | Glu | Ala | Phe | His<br>335 | Val |
| Gly | Lys | Thr | Pro<br>340 | Ile | Val | Gly | Gln | Pro<br>345 | Ser | Val | Pro | Gly | Gly<br>350 | Pro | Val |
| His | Leu | Cys<br>355 | Pro | Gly | Arg | Ile | Arg<br>360 | Tyr | Phe | Lys | Ile | | | | |

( 2 ) INFORMATION FOR SEQ ID NO:11:

( i ) SEQUENCE CHARACTERISTICS:
        ( A ) LENGTH: 352 amino acids
        ( B ) TYPE: amino acid
        ( C ) STRANDEDNESS: single
        ( D ) TOPOLOGY: linear ( i i ) MOLECULE TYPE: peptide (v i) ORIGINAL SOURCE:
  (A) ORGANISM: Rat (x i) SEQUENCE DESCRIPTION: SEQ ID NO:11:

| | | | | | | | | | | | | | | |
|---|---|---|---|---|---|---|---|---|---|---|---|---|---|---|
| Met | Lys | Ser | Leu | Val | Leu | Leu | Cys | Phe | Ala | Gln | Leu | Trp | Ser | Cys |
| 1 | | | | 5 | | | | | 10 | | | | | 15 |
| Gln | Ser | Ala | Pro | Gln | Gly | Ala | Gly | Leu | Gly | Phe | Arg | Glu | Leu | Ala | Cys |
| | | | 20 | | | | 25 | | | | | 30 | | |
| Asp | Asp | Pro | Glu | Thr | Glu | His | Val | Ala | Leu | Ile | Ala | Val | Asp | Tyr | Leu |
| | | 35 | | | | 40 | | | | | 45 | | | |
| Asn | Lys | His | Leu | Leu | Gln | Gly | Phe | Arg | Gln | Ile | Leu | Asn | Gln | Ile | Asp |
| | 50 | | | | 55 | | | | | 60 | | | |
| Lys | Val | Lys | Val | Trp | Ser | Arg | Arg | Pro | Phe | Gly | Glu | Val | Tyr | Glu | Leu |
| 65 | | | | 70 | | | | | 75 | | | | | 80 |
| Glu | Ile | Asp | Thr | Leu | Glu | Thr | Thr | Cys | His | Ala | Leu | Asp | Pro | Thr | Pro |
| | | | 85 | | | | 90 | | | | | 95 | | |
| Leu | Ala | Asn | Cys | Ser | Val | Arg | Gln | Gln | Ala | Glu | His | Ala | Val | Glu | Gly |
| | | | 100 | | | | 105 | | | | | 110 | | |
| Asp | Cys | Asp | Phe | His | Ile | Leu | Lys | Gln | Asp | Gly | Gln | Phe | Arg | Val | Leu |
| | | 115 | | | | 120 | | | | | 125 | | | |
| His | Ala | Gln | Cys | His | Ser | Thr | Pro | Asp | Ser | Ala | Glu | Asp | Val | Arg | Lys |
| | 130 | | | | 135 | | | | | 140 | | | |
| Phe | Cys | Pro | Arg | Cys | Pro | Ile | Leu | Ile | Arg | Phe | Asn | Asp | Ile | Asn | Val |
| 145 | | | | 150 | | | | | 155 | | | | | 160 |
| Val | His | Thr | Val | Lys | Thr | Ala | Leu | Ala | Ala | Phe | Asn | Ala | Gln | Asn | Asn |
| | | | 165 | | | | 170 | | | | | 175 | | |
| Gly | Thr | Tyr | Phe | Lys | Leu | Val | Glu | Ile | Ser | Arg | Ala | Gln | Asn | Val | Pro |
| | | | 180 | | | | 185 | | | | | 190 | | |
| Phe | Pro | Val | Ser | Thr | Leu | Val | Glu | Phe | Val | Ile | Ala | Ala | Thr | Asp | Cys |
| | | 195 | | | | 200 | | | | | 205 | | | |
| Thr | Gly | Gln | Glu | Val | Thr | Asp | Pro | Ala | Lys | Cys | Asn | Leu | Leu | Ala | Glu |
| | 210 | | | | 215 | | | | | 220 | | | |
| Lys | Gln | Tyr | Gly | Phe | Cys | Lys | Ala | Thr | Leu | Ile | His | Arg | Leu | Gly | Gly |
| 225 | | | | 230 | | | | | 235 | | | | | 240 |
| Glu | Glu | Val | Ser | Val | Ala | Cys | Lys | Leu | Phe | Gln | Thr | Gln | Pro | Gln | Pro |
| | | | 245 | | | | 250 | | | | | 255 | | |
| Ala | Asn | Ala | Asn | Pro | Ala | Gly | Pro | Ala | Pro | Thr | Tyr | Gly | Gln | Ala | Ala |
| | | | 260 | | | | 265 | | | | | 270 | | |
| Pro | Val | Ala | Pro | Pro | Ala | Gly | Pro | Glu | Ser | Val | Val | Gly | Pro |
| | | 275 | | | | 280 | | | | | 285 | | | |
| Val | Ala | Val | Pro | Leu | Gly | Leu | Pro | Asp | His | Arg | Thr | His | His | Asp | Leu |
| | 290 | | | | 295 | | | | | 300 | | | |
| Arg | His | Ala | Phe | Ser | Pro | Val | Ala | Ser | Val | Glu | Ser | Ala | Ser | Gly | Glu |
| 305 | | | | 310 | | | | | 315 | | | | | 320 |
| Val | Leu | His | Ser | Pro | Lys | Val | Gly | Gln | Pro | Gly | Asp | Ala | Gly | Ala | Ala |
| | | | 325 | | | | 330 | | | | | 335 | | |
| Gly | Pro | Val | Ala | Pro | Leu | Cys | Pro | Gly | Arg | Val | Arg | Tyr | Phe | Lys | Ile |
| | | | 340 | | | | 345 | | | | | 350 | | |

(2) INFORMATION FOR SEQ ID NO:12:

(i) SEQUENCE CHARACTERISTICS:
    (A) LENGTH: 349 amino acids
    (B) TYPE: amino acid
    (C) STRANDEDNESS: single
    (D) TOPOLOGY: linear (ii) MOLECULE TYPE: peptide (vi) ORIGINAL SOURCE:
(A) ORGANISM: Homo sapiens (xi) SEQUENCE DESCRIPTION: SEQ ID NO:12:

```
Ala Pro His Gly Pro Gly Leu Ile Tyr Arg Gln Pro Asn Cys Asp Asp
1               5                   10                  15
Pro Glu Thr Glu Glu Ala Ala Leu Val Ala Ile Asp Tyr Ile Asn Gln
            20                  25                  30
Asn Leu Pro Trp Gly Tyr Lys His Thr Leu Asn Gln Ile Asp Glu Val
            35                  40                  45
Lys Val Trp Pro Gln Gln Pro Ser Gly Glu Leu Glu Glu Ile Glu Ile
        50                  55                  60
Asp Thr Leu Glu Thr Thr Cys His Val Leu Asp Pro Thr Pro Val Ala
65                  70                  75                  80
Arg Cys Ser Val Arg Gln Leu Lys Glu His Ala Val Glu Gly Asp Cys
                85                  90                  95
Asp Phe Gln Leu Leu Lys Leu Asp Gly Lys Phe Ser Val Val Tyr Ala
                100                 105                 110
Lys Cys Asp Ser Ser Pro Asp Ser Ala Glu Asp Val Arg Lys Val Cys
            115                 120                 125
Gln Asp Cys Pro Leu Leu Ala Pro Leu Asn Asp Thr Arg Val Val His
        130                 135                 140
Ala Ala Lys Ala Ala Leu Ala Ala Phe Asn Ala Gln Asn Asn Gly Ser
145                 150                 155                 160
Asn Phe Gln Leu Glu Glu Ile Ser Arg Ala Gln Leu Val Pro Leu Pro
                165                 170                 175
Pro Ser Thr Tyr Val Glu Phe Thr Val Ser Gly Thr Asp Cys Val Ala
                180                 185                 190
Lys Glu Ala Thr Glu Ala Ala Lys Cys Asn Leu Leu Ala Glu Lys Gln
            195                 200                 205
Tyr Gly Pro Cys Lys Ala Thr Leu Ser Glu Lys Leu Gly Gly Ala Glu
        210                 215                 220
Val Ala Val Thr Cys Thr Val Phe Gln Thr Gln Pro Val Thr Ser Gln
225                 230                 235                 240
Pro Gln Pro Glu Gly Ala Asn Glu Ala Val Pro Thr Pro Val Val Asp
                245                 250                 255
Pro Asp Ala Pro Pro Ser Pro Pro Leu Gly Ala Pro Gly Leu Pro Pro
            260                 265                 270
Ala Gly Ser Pro Pro Asp Ser His Val Leu Leu Ala Ala Pro Pro Gly
            275                 280                 285
His Gln Leu His Arg Ala His Tyr Asp Leu Arg His Thr Phe Met Gly
    290                 295                 300
Val Val Ser Leu Gly Ser Pro Ser Gly Glu Val Ser His Pro Arg Lys
305                 310                 315                 320
Thr Arg Thr Val Val Gln Pro Ser Val Gly Ala Ala Ala Gly Pro Val
                325                 330                 335
Val Pro Pro Cys Pro Gly Arg Ile Arg His Phe Lys Val
            340                 345
```

(2) INFORMATION FOR SEQ ID NO:13:

(i) SEQUENCE CHARACTERISTICS:
(A) LENGTH: 31 amino acids
(B) TYPE: amino acid
(C) STRANDEDNESS: single -continued (D) TOPOLOGY: linear (ii) MOLECULE TYPE: peptide (xi) SEQUENCE DESCRIPTION: SEQ ID NO:13:

```
Cys Gly Asn Glu Asp His Cys Glu Gly Gln Gln Cys Phe Ser Ser Leu
 1               5                  10                  15

Ser Ile Tyr Asp Gly Phe His Val Tyr Gln Lys Gly Cys Phe Gln
            20                  25                  30
```